(12) United States Patent
Glukhovsky et al.

(10) Patent No.: US 9,925,374 B2
(45) Date of Patent: Mar. 27, 2018

(54) TREATMENT OF INDICATIONS USING ELECTRICAL STIMULATION

(75) Inventors: Arkady Glukhovsky, Santa Clarita, CA (US); Mark L. Lindon, Calabasas, CA (US); Yitzhak Zilberman, Santa Clarita, CA (US)

(73) Assignee: Bioness Inc., Valencia, CA (US)

( * ) Notice: Subject to any disclaimer, the term of this patent is extended or adjusted under 35 U.S.C. 154(b) by 387 days.

(21) Appl. No.: 13/000,840

(22) PCT Filed: Jun. 24, 2009
(Under 37 CFR 1.47)

(86) PCT No.: PCT/US2009/048419
§ 371 (c)(1),
(2), (4) Date: May 26, 2011

(87) PCT Pub. No.: WO2009/158389
PCT Pub. Date: Dec. 30, 2009

(65) Prior Publication Data
US 2011/0282412 A1 Nov. 17, 2011

Related U.S. Application Data

(63) Continuation-in-part of application No. 12/147,937, filed on Jun. 27, 2008, now abandoned.

(51) Int. Cl.
*A61N 1/36* (2006.01)
*A61N 1/375* (2006.01)

(52) U.S. Cl.
CPC .......... *A61N 1/36007* (2013.01); *A61N 1/375* (2013.01)

(58) Field of Classification Search
CPC ............ A61N 1/36021; A61N 1/36071; A61N 1/326; A61N 1/36017; A61N 1/025;
(Continued)

(56) References Cited

U.S. PATENT DOCUMENTS 3,204,637 A 9/1965 Frank et al.
3,426,748 A 2/1969 Bowers
(Continued)

FOREIGN PATENT DOCUMENTS

CA 2484310 11/2003
EP 0862925 9/1998
(Continued)

OTHER PUBLICATIONS

International Search Report and Written Opinion for International Application No. PCT/US10/58525, dated Feb. 7, 2011.
(Continued)

*Primary Examiner* — Amanda Patton
(74) *Attorney, Agent, or Firm* — Cooley LLP

(57) ABSTRACT

In one embodiment, a method includes implanting an implant entirely under the subject's skin. The implant includes a passive electrical conductor of sufficient length to extend from subcutaneous tissue located below one of a surface cathodic electrode and a surface anodic electrode to the tibial nerve. The surface electrodes are positioned in spaced relationship on the subject's skin, with one of the electrodes positioned over the pick-up end of the electrical conductor such that the portion of the current is transmitted through the conductor to the tibial nerve, and such that the current flows through the tibial nerve and returns to the other of the surface cathodic electrode and the surface anodic electrode. An electrical current is applied between the surface cathodic electrode and the surface anodic electrode to cause the portion of the electrical current to flow through the implant to stimulate the tibial nerve.

18 Claims, 15 Drawing Sheets

(58) Field of Classification Search
CPC .. A61N 1/0456; A61N 1/3752; A61N 1/3756; A61N 1/048; A61N 1/0492; A61N 1/375
USPC ..................................................... 607/41, 46
See application file for complete search history.

(56) References Cited

U.S. PATENT DOCUMENTS

| | | | |
|---|---|---|---|
| 3,774,618 A | 11/1973 | Avery | |
| 3,835,864 A | 9/1974 | Rasor et al. | |
| 3,964,470 A | 6/1976 | Trombley | |
| 3,995,644 A | 12/1976 | Parsons | |
| 4,102,344 A | 7/1978 | Conway et al. | |
| 4,323,999 A | 4/1982 | Yoshizawa et al. | |
| 4,417,888 A | 11/1983 | Cosentino et al. | |
| 4,419,995 A | 12/1983 | Hochmair et al. | |
| 4,793,353 A | 12/1988 | Borkan | |
| 4,922,927 A | 5/1990 | Fine et al. | |
| 4,987,897 A | 1/1991 | Funke | |
| 5,080,099 A | 1/1992 | Way et al. | |
| 5,098,397 A | 3/1992 | Svensson et al. | |
| 5,325,870 A | 7/1994 | Kroll et al. | |
| 5,330,516 A | 7/1994 | Nathan | |
| 5,356,428 A | 10/1994 | Way | |
| 5,441,518 A | 8/1995 | Adams et al. | |
| 5,441,527 A | 8/1995 | Erickson et al. | |
| 5,443,065 A | 8/1995 | Berghoff et al. | |
| 5,465,715 A | 11/1995 | Lyons | |
| RE35,129 E | 12/1995 | Pethica et al. | |
| 5,531,782 A | 7/1996 | Kroll et al. | |
| 5,562,707 A | 10/1996 | Prochazka et al. | |
| 5,571,148 A | 11/1996 | Loeb et al. | |
| 5,578,065 A | 11/1996 | Hattori et al. | |
| 5,674,253 A | 10/1997 | Adams et al. | |
| 5,702,428 A | 12/1997 | Tippey et al. | |
| 5,766,231 A | 6/1998 | Erickson et al. | |
| 5,776,178 A | 7/1998 | Pohndorf et al. | |
| 5,782,645 A | 7/1998 | Stobie et al. | |
| 5,796,827 A | 8/1998 | Coppersmith et al. | |
| 5,807,397 A | 9/1998 | Barreras | |
| 5,843,132 A | 12/1998 | Ilvento | |
| 5,914,701 A | 6/1999 | Gersheneld et al. | |
| 5,916,244 A | 6/1999 | Walters | |
| 5,948,006 A | 9/1999 | Mann | |
| 6,006,122 A | 12/1999 | Smits et al. | |
| 6,076,016 A | 6/2000 | Feierbach | |
| 6,214,032 B1 | 4/2001 | Loeb et al. | |
| 6,233,488 B1 | 5/2001 | Hess | |
| 6,259,952 B1 | 7/2001 | Sluijter et al. | |
| 6,266,567 B1 | 7/2001 | Ishikawa et al. | |
| 6,292,699 B1 | 9/2001 | Simon et al. | |
| 6,351,674 B2 | 2/2002 | Silverstone | |
| 6,366,814 B1 | 4/2002 | Boveja et al. | |
| 6,393,323 B1 | 5/2002 | Sawan | |
| 6,415,184 B1 | 7/2002 | Ishikawa et al. | |
| 6,505,074 B2 | 1/2003 | Boveja | |
| 6,505,082 B1 | 1/2003 | Scheiner et al. | |
| 6,564,102 B1 | 5/2003 | Boveja | |
| 6,607,500 B2 | 8/2003 | Da Silva et al. | |
| 6,668,191 B1 | 12/2003 | Boveja | |
| 6,735,474 B1 | 5/2004 | Loeb et al. | |
| 6,735,475 B1 | 5/2004 | Whitehurst et al. | |
| 6,754,472 B1 | 6/2004 | Williams et al. | |
| 6,829,508 B2 | 12/2004 | Schulman et al. | |
| 6,840,919 B1 | 1/2005 | Håkansson | |
| 6,847,844 B2 | 1/2005 | Sun et al. | |
| 6,879,859 B1 | 4/2005 | Boveja | |
| 6,892,098 B2 | 5/2005 | Ayal et al. | |
| 6,896,675 B2 | 5/2005 | Leung et al. | |
| 6,928,320 B2 | 8/2005 | King | |
| 6,941,171 B2 | 9/2005 | Mann et al. | |
| 6,961,623 B2 | 11/2005 | Prochazka | |
| 7,013,179 B2 | 3/2006 | Carter et al. | |
| 7,047,071 B2 | 5/2006 | Wagner et al. | |
| 7,162,303 B2 | 1/2007 | Levin et al. | |
| 7,324,853 B2 | 1/2008 | Ayal et al. | |
| 7,389,145 B2 | 6/2008 | Kilgore et al. | |
| 7,415,309 B2 | 8/2008 | McIntyre | |
| 7,502,652 B2 | 3/2009 | Gaunt et al. | |
| 7,536,226 B2 | 5/2009 | Williams et al. | |
| 9,072,886 B2 | 7/2015 | Gaunt et al. | |
| 9,072,896 B2 | 7/2015 | Dar et al. | |
| 2001/0002441 A1 | 5/2001 | Boveja | |
| 2001/0047167 A1 | 11/2001 | Heggeness | |
| 2002/0055761 A1 | 5/2002 | Mann et al. | |
| 2002/0055779 A1 | 5/2002 | Andrews | |
| 2002/0077831 A1 | 6/2002 | Numa | |
| 2002/0111663 A1 | 8/2002 | Dahl et al. | |
| 2003/0028232 A1 | 2/2003 | Camps et al. | |
| 2003/0078642 A1 | 4/2003 | Malaney et al. | |
| 2003/0139794 A1 | 7/2003 | Jenney et al. | |
| 2003/0171792 A1 | 9/2003 | Zarinetchi et al. | |
| 2003/0181090 A1 | 9/2003 | Ehr et al. | |
| 2003/0199807 A1 | 10/2003 | Dent et al. | |
| 2003/0212395 A1 | 11/2003 | Woloszko et al. | |
| 2003/0212440 A1 | 11/2003 | Boveja | |
| 2003/0236557 A1 | 12/2003 | Whitehurst et al. | |
| 2004/0049235 A1 | 3/2004 | Deno et al. | |
| 2004/0130455 A1* | 7/2004 | Prochazka | 340/825.19 |
| 2004/0176804 A1 | 9/2004 | Palti | |
| 2004/0267333 A1* | 12/2004 | Kronberg | 607/72 |
| 2005/0070970 A1 | 3/2005 | Knudson et al. | |
| 2005/0136385 A1 | 6/2005 | Mann et al. | |
| 2005/0165461 A1 | 7/2005 | Takeda et al. | |
| 2006/0064140 A1 | 3/2006 | Whitehurst et al. | |
| 2006/0184211 A1* | 8/2006 | Gaunt et al. | 607/48 |
| 2006/0206165 A1 | 9/2006 | Jaax et al. | |
| 2006/0271118 A1 | 11/2006 | Libbus et al. | |
| 2007/0088419 A1 | 4/2007 | Fiorina et al. | |
| 2008/0004676 A1 | 1/2008 | Osypka et al. | |
| 2008/0033510 A1* | 2/2008 | Herregraven et al. | 607/63 |
| 2008/0046053 A1 | 2/2008 | Wagner et al. | |
| 2008/0243216 A1 | 10/2008 | Zilberman et al. | |
| 2009/0054952 A1 | 2/2009 | Glukhovsky et al. | |
| 2009/0149917 A1 | 6/2009 | Whitehurst et al. | |
| 2009/0222053 A1 | 9/2009 | Gaunt | |
| 2009/0326602 A1 | 12/2009 | Glukhovsky et al. | |
| 2010/0016929 A1 | 1/2010 | Prochazka | |
| 2010/0076533 A1 | 3/2010 | Dar et al. | |
| 2010/0198298 A1 | 8/2010 | Glukhovsky et al. | |
| 2013/0138164 A1 | 5/2013 | Dar et al. | |
| 2015/0165186 A1 | 6/2015 | Dar et al. | |

FOREIGN PATENT DOCUMENTS

| | | | |
|---|---|---|---|
| JP | 62-286471 | 12/1987 | |
| JP | 07-308392 | 11/1995 | |
| JP | 09-276418 | 10/1997 | |
| JP | 10-509901 | 9/1998 | |
| JP | 2003-501207 | 1/2003 | |
| JP | 2005-237941 | 9/2005 | |
| JP | 2009-529352 | 8/2009 | |
| WO | WO 95/10323 | 4/1995 | |
| WO | WO 00/57950 | 10/2000 | |
| WO | WO 01/003768 | 1/2001 | |
| WO | WO 04/052450 | 6/2004 | |
| WO | WO 05/007120 | 1/2005 | |
| WO | WO 05/37367 | 4/2005 | |
| WO | WO 05/70494 | 8/2005 | |
| WO | WO 06/101917 | 9/2006 | |
| WO | WO 06/113654 | 10/2006 | |
| WO | WO 06/113801 | 10/2006 | |
| WO | WO 07/002741 | 1/2007 | |
| WO | WO 07/008906 | 1/2007 | |
| WO | WO 2007002741 A1 * | 1/2007 | A61N 1/34 |
| WO | WO 07/82382 | 7/2007 | |
| WO | WO 08/140242 | 11/2008 | |
| WO | WO 09/058258 | 5/2009 | |
| WO | WO 2011/068849 | 6/2011 | |

OTHER PUBLICATIONS

International Search Report and Written Opinion for International Application No. PCT/US2009/048419, dated Aug. 18, 2009.

(56) References Cited

OTHER PUBLICATIONS

Office Action for European Patent Application EP 05700290.9, dated Jun. 16, 2009.
Partial Translation of Office Action for Japanese Patent Application No. JP 2004-543869, dated May 26, 2009.
Supplementary European Search Report for European Patent Application EP 05700290.9, dated Jan. 27, 2009.
Supplementary European Search Report for European Patent Application EP 07701705.1, dated Jun. 7, 2010.
International Search Report and Written Opinion for PCT/CA2010/001487, dated Jan. 18, 2011.
Abel-Gawad, M. et. al., "Reduction of bladder outlet resistance by selective stimulation of the ventral sacral root using high frequency blockage: a chronic study in spinal cord transected dogs," Journal of Urology, vol. 166 (2001), pp. 728-733.
Apkarian, J.A. et al., "Stretch reflex inhibition using electrical stimulation in normal subjects and subjects with spasticity," Journal of Biomedical Engineering, vol. 13 (1991), pp. 67-73.
Ashkan, K. et al., "Deep brain stimulation of the subthalamic nucleus in Parkinson's disease 1993-2003: where are we 10 years on?," Br J. Neurosurg, vol. 18 (2004), pp. 19-34.
Benabid, A.L. et al., "Combined (Thalamotomy and stimulation) stereotactic surgery of the VIM thalamic nucleus for bilateral Parkinson disease," Applied Neurophysiology, vol. 50 (1987), pp. 344-346.
Bhadra, N. et al., "High-frequency electrical conduction block of mammalian peripheral motor nerve," Muscle & Nerve (Epub ahead of Dec. 2005 print) (2005), pp. 782-790.
Brindley, G.S. et al., "Sacral anterior root stimulators for bladder control in paraplegia," Paraplegia, vol. 20 (1982), pp. 365-381.
Broseta, J. et al., "High-frequency cervical spinal cord stimulation in spasticity and motor disorders," Acta Neurochir Suppl (Wien), vol. 39 (1987), pp. 106-111.
Filali, M. et al., "Stimulation-induced inhibition of neuronal firing in human subthalamic nucleus," Exp Brain Res, vol. 156(3) (2004), pp. 274-281.
Glenn, W.W. et al., "Radiofrequency-controlled catheter pacemaker, Clinical application," New England Journal of Medicine, vol. 275 (1966), pp. 137-140.
Grill, W.M., Jr. et al., "Quantification of recruitment properties of multiple contact cuff electrodes," IEEE Trans. Rehabil. Eng., vol. 4(2) (1996), pp. 49-62.
Groen, J. et al., "Neuromodulation techniques in the treatment of the overactive bladder," BJU Int, vol. 87(8) (2001), pp. 723-731.
Handa, Y. et al., "Application of functional electrical stimulation to the paralyzed extremities," Neurologia Medico-Chirurgica, vol. 38 (1998), pp. 784-788.
Haugland, M., et al. Interfacing the body's own sensing receptors into neural prosthesis devices. Technology Health Care, vol. 7 (1999), pp. 393-399.
Kilgore, K.L., et al. Chapter 6.2: Upper and lower extremity motor neuroprostheses. in Horch, K.W. and Dhillon, G.S., ed. Neuroprosthetics. Theory and Practice, vol. 2 World Scientific, New Jersey (2004), pp. 844-877.
Kilgore, K.L., et al. Block of Nerve Conduction Using High Frequency Alternating Current. 9th Annual Conference of the International FES Society, Sep. 2004—Bournemouth, UK (2004).
Kralj, A.R. et al., "Functional Electrical Stimulation: Standing and Walking after Spinal Cord Injury," CRC Press, Boca Raton, FL (1989), pp. 1-15.
Landau, B. et al., "Neuromodulation techniques for medically refractory chronic pain," Annu Rev Med vol. 44 (1993), pp. 279-287.
Peckham et al., "Restoration of key grip and release in the C6 tetraplegic patient through functional electrical stimulation," The Journal of Hand Surgery, vol. 5, No. 5 (Sep. 1980), pp. 462-469.
Peckham, P.H. et al., "Implantable Neuroprosthesis Research G Efficacy of an implanted neuroprosthesis for restoring hand grasp in tetraplegia: a multicenter study," Archives of Physical Medicine & Rehabilitation vol. 82 (2001), pp. 1380-1388.
Prochazka, A. et al., "The Bionic glove: an electrical stimulator garment that provides controlled grasp and hand opening in quadriplegia," Arch. Phys. Med. Rehabil. vol. 78 (1997), pp. 608-614.
Shaker, H. et al., "Sacral root neuromodulation in the Treatment of Various Voiding and Storage Problems," International Urogynecology Journal vol. 10 (1999), pp. 336-343.
Shaker, H.S. et al., "Reduction of bladder outlet resistance by selective sacral root stimulation using high-frequency blockade in dogs: an acute study," J Urol 160 (3 Pt 1) (1997), pp. 901-907.
Solomonow, M. et al., "Control of muscle contractile force through indirect high-frequency stimulation," Am J Phys Med, vol. 62 (1983), pp. 71-82.
Strojnik, P. et al., "Treatment of drop foot using an implantable peroneal underknee stimulator," Scandanavian J. of Rehabil. Med., vol. 19 (1987), pp. 37-43.
Tai, C. et al., "Block of external urethral sphincter contradiction by high frequency electrical stimulation of pudendal nerve," J Urol, vol. 172 (5 Pt 1) (2004), pp. 2069-2072.
Tai, C. et al., "Response of external urethral sphincter to high frequency biphasic electrical stimulation of pudendal nerve," J Urol, vol. 174(2) (2005), pp. 782-786.
Van Heeckeren, D.W. et al., "Electrophrenic respiration by radiofrequency induction," Journal of Thoracic & Cardiovascular Surgery, vol. 52 (1966), pp. 655-665.
Vodovnik, L., "Therapeutic effects of functional electrical stimulation of extremities," Medical and Biological Engineering & Computing, vol. 19 (1981), pp. 470-478.
Walker, J. et al., "Fundamentals of Physics," New Jersey, Hoboken, (2007), pp. 791-817.
Waltz, J.M., "Spinal cord stimulation: a quarter century of development and investigation. A review of its development and effectiveness in 1,336 cases," Stereotactic & Functional Neurosurgery, vol. 69 (1997), pp. 288-299.
Yu, D.T. et al., "Percutaneous intramuscular neuromuscular electric stimulation for the treatment of shoulder subluxation and pain in patients with chronic hemiplegia: a pilot study," Arch Phys Med Rehabil, vol. 82 (1997), pp. 20-25.
Grill, W., "Percutaneous Stimulation a Potential Incontinence Option," Neurotech business report [online] [retrieved on Apr. 11, 2008] Retrieved from the Internet: <URL:http://www.neurotechreports.com/pages/PerQstimulation.html> 2 pages.
The Regence Group Medical Policy—Surgery Section—Posterior Tibial Nerve Stimulation for Voiding Dysfunction [online] [retrieved on Apr. 11, 2008] Retrieved from the Internet: <URL: http://www.regence.com/trgmedpol/surgery/sur154.html> 3 pages.
CystoMedix, Inc., "Percutaneous Tibial Nerve Stimulation via Urgent® PC Neuromodulation System—An Emerging Technology for Managing Overactive Bladder."
Amerenco, G. et al., "Urodynamic Effect of Acute Transcutaneous Posterior Tibial Nerve Stimulation in Overactive Bladder," The Journal of Urology, vol. 169 (Jun. 2003), pp. 2210-2215.
Vandoninck, V. et al., "Posterior Tibial Nerve Stimulation in the Treatment of Urge Incontinence," (Abstract), Neurology and Urodynamics. [online] [Retrieved on Apr. 11, 2008] Retrieved from the Internet: <URL: http://cat.inist.fr/?aModele=afficheN&cpsidt=14431487> 1 page.
Bionicare Press Release, "New Data Suggest Electrical Stimulation Can Defer Total Knee Replacement Surgery in Patients With Osteoarthritis," (Mar. 10, 2004), 2 pages.
"Using Electrical Stimulation to Put Off Having a Total Knee Replacement," [online] [Retrieved on Apr. 11, 2008] Retrieved from the Internet: <URL:http://www.eorthopod.com/public/patient_education/6330/using_electrical_stimulation_to_put_off_havi . . . > 3 pages.
Stevens, J. E. et al., "Neuromuscular electrical stimulation for quadriceps muscle strengthening after bilateral total knee arthroplasty: a case series," (Abstract), J Orthop Sports Phys Ther. (Jan. 2004), 1 page.
Snyder-Mckler, L. et al., "Strength of the quadriceps femoris muscle and functional recovery after reconstruction of the anterior cruciate ligament. A prospective, randomized clinical trial of electrical stimulation," The Journal of Bone and Joint Surgery (abstract)

(56) References Cited

OTHER PUBLICATIONS

[online] [Retrieved on Apr. 11, 2008] Retrieved from the Internet: <URL:http://www.ejbjs.org/cgi/content/abstract/77/8/1166> 5 pages.
Gotlin, R. S. et al., "Electrical stimulation effect on extensor lag and length of hospital stay after total knee arthroplasty," Arch Phys Med Rehabil, (Sep. 1994) (abstract) [online] [Retrieved on Apr. 11, 2008] Retrieved from: PubMed, PMID: 8085929.
Campbell, J. M., "Electrical Stimulation in Orthopaedic Disability," Jun. 2002, 3 pages.
Finsen, V., "Transcutaneous Electrical Nerve Stimulation After Major Amputation," The Journal of Bone and Joint Surgery, vol. 70-B, No. 1 (Jan. 1988), pp. 109-112.
The-Health-Pages.com—General Adult Health Information, "Total Knee Replacement (also called Total Knee Arthroplasty)," [online] [Retrieved on Apr. 11, 2008] Retrieved from the Internet: <URL: http://www.the-health-pages.com/topics/education/tkr.html> 9 pages.
Ifess, "Electrical Stimulation and Wound Healing References," [online] [Retrieved on Sep. 10, 2007] Retrieved from the Internet: <URL: http://www.ifess.org/services/consumer-ed/references/wound-healing_references.htm>.
Stoykov et al., "Recording Intramuscular EMG Signals Using Surface Electrodes, 2005 IEEE 9th International Conference on Rehabilitation Robotics," Jun. 28-Jul. 1, 2005, Chicago, IL, pp. 291-294.
Prochazka et al., "Clinical experience with reinforced, anchored intramuscular electrodes for functional neuromuscular stimulation," Journal of Neuroscience Methods, vol. 42 (1992), pp. 175-184.
Melzack et al., "Pain Mechanisms: A New Theory," Science, vol. 150 (Nov. 19, 1965), No. 3699, pp. 971-979.
Tagusari et al., "Fine Trabecularized Carbon: Ideal Material and Texture for Percutaneous Device System of Permanent Left Ventricular Assist Device. Artificial Organs," vol. 22, No. 6 (Jun. 1998), pp. 481-487.
Marsolais et al., "Implantation techniques and experience with percutaneous intramuscular electrodes in the lower extremities," Journal of Rehabilitation Research and Development, Veterans Administration, vol. 3, No. 3, pp. 1-8.
Masini et al., "Activated Pyrolytic Carbon Tip Pacing Leads: An Alternative to Steriod-Eluting Pacing Leads?" Pacing and Clinical Electrophysiology, vol. 19, No. 11 (Nov. 1996), pp. 1832-1835.
"Innovative Medical Devices for Neuro-Technologies," NeuroTECH, [online] [Retrieved on Sep. 21, 2007] Retrieved from the Internet: <URL: http://www.neurotech.be/Prod_cuffelectrode.htm>.
Gans, L. et al., "The Stimulus Router: A Novel Means of Directing Current From Surface Electrodes to Nerves," 10th Annual Conference of the International FES Society (Jul. 2005), Montreal, Canada, pp. 21-23.
Gans et al., "The Stimulus Router: A Novel Means of Directing Current From Surface Electrodes to Nerves," 10th Annual Conference of the International FES Society (Jul. 2005), Montreal, Canada, Display Poster.
Bhadra, N. et al., "Direct Current Electrical Conduction Block of Peripheral Nerve. IEEE Transactions on Neural Systems and Rehabilitation Engineering," vol. 12, No. 3 (Sep. 2004), pp. 313-324.
Cattell, M. et al., "The 'Inhibitory' Effect of High-Frequency Stimulation and the Excitation State of Nerve," Department of Physiology, Unversity College, London (Nov. 1934), pp. 407-415.
Tai, C. et al., "Voiding Reflex in Chronic Spinal Cord Injured Cats Induced by Stimulating and Blocking Pudendal Nerves," Department of Pharmacology, University of Pittsburgh (2007), Neurourology and Urodynamics 26, pp. 879-886.
Woo, R., "Spasticity: Orthopedic Perspective," (2001) Special Article, Journal of Child Neurology, vol. 16, No. 1, pp. 47-53.
Skold, C. et al., "Spasticity After Traumatic Spinal Cord Injury: Nature, Severity, and Location," Arch Phys Med Rehabil, vol. 80 (Dec. 1999), pp. 1548-1557.
Whitwam, J. G. et al., "The Use of Direct Current to Cause Selective Block of Large Fibres in Peripheral Nerves," Br. J. Anaesth. (1975), vol. 47, pp. 1123-1133.
Amis, A. et al., "Relative Displacements in Muscle and Tendon During Human Arm Movements," J. Physiol. (1987), vol. 389, pp. 37-44.
Scheiner, A. et al., "Imbalanced Biphasic Electrical Stimulation: Muscle Tissue Damage," Annals of Biomedical Engineering (1990), vol. 18, pp. 407-425.
Ade-Hall, R. et al., "Botulinum toxin type A in the treatment of lower limb spasticity in cerebral palsy (Review)," The Cochrane Library (2009), Issue 3, 19 pages.
Merrill, D. et al., "Electrical stimulation of excitable tissue: design of efficacious and safe protocols," Journal of Neuroscience Methods vol. 141 (2005), pp. 171-198.
Jankovic, J., M.D. et al., "Outcome after Stereotactic Thalamotomy for Parkinsonian, Essential, and Other Types of Tremor," Neurosurgery Online [online] [retrieved on May 21, 2009] Retrieved from the Internet: <URL:http://www.ovidsp.tx.ovid.com/spa/ovidweb.cgi?&S=AACMFPFHBADDKOHCNCFLGDMJJ . . . I> 9 pages.
McCreery, D. et al., "Charge Density and Charge Per Phase as Cofactors in Neural Injury Induced by Electrical Stimulation," IEEE Transactions on Biomedical Engineering, vol. 37, No. 10 (Oct. 1990), pp. 996-1001.
Supplementary Search Report for European Patent Application No. 09770922.4; dated Jan. 5, 2012.
Office Action for U.S. Appl. No. 11/993,393; dated Nov. 2, 2011.
Office Action for U.S. Appl. No. 12/400,202, dated Mar. 5, 2012.
Office Action for U.S. Appl. No. 12/400,202, dated Aug. 8, 2012.
Office Action for Canadian Application No. 2,608,397, dated Jan. 25, 2013.
Office Action for Australian Application No. 2009262237, dated Aug. 12, 2013.
Office Action for Japanese Application No. 2011-516572, dated Jun. 21, 2013.
Office Action for Japanese Application No. 2011-516572, dated Jan. 28, 2014.
Office Action for Canadian Application No. 2,727,812, dated Nov. 9, 2016, 5 pages.

\* cited by examiner

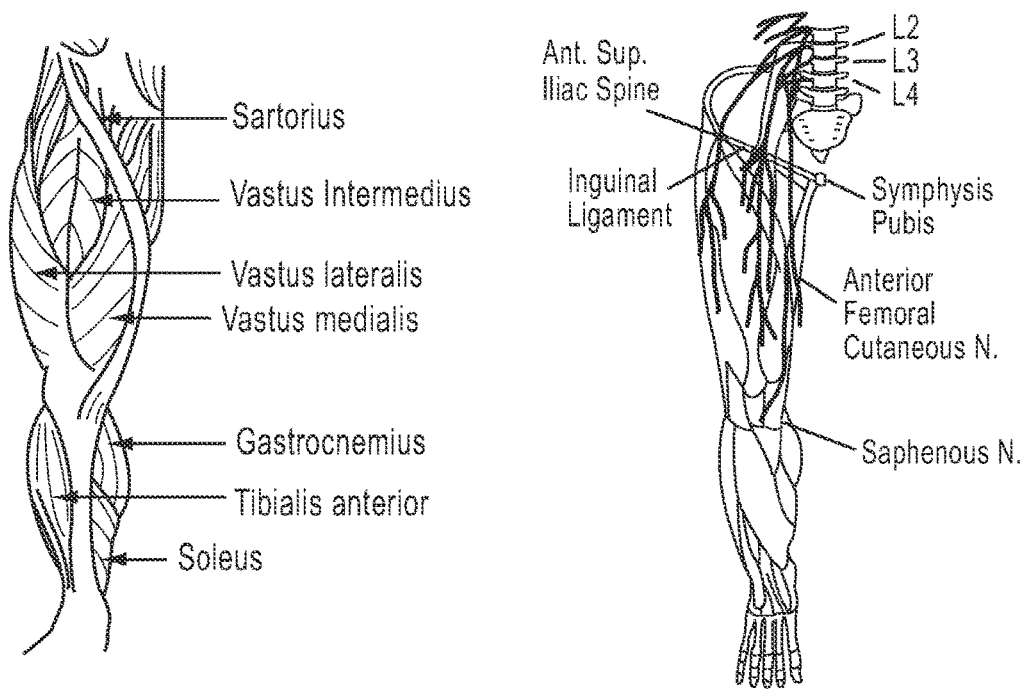
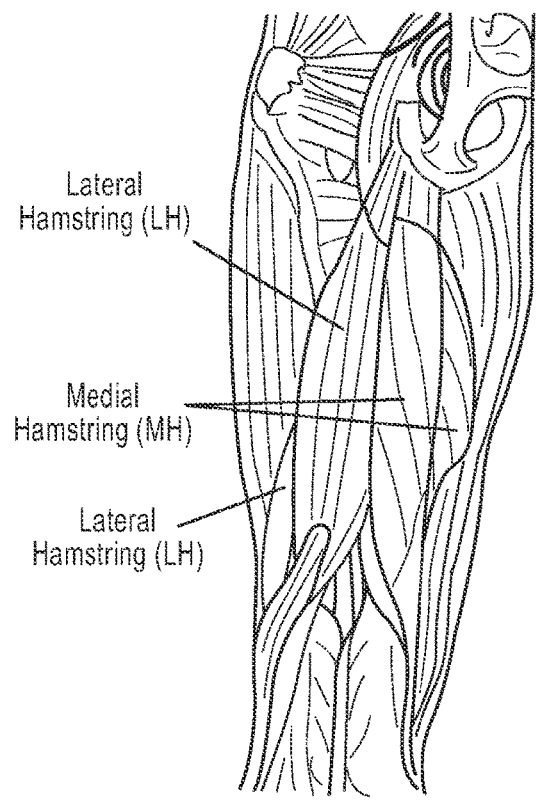
FIG.2
FIG.3

TREATMENT OF INDICATIONS USING ELECTRICAL STIMULATION

CROSS-REFERENCE TO RELATED APPLICATIONS

The application is a 35 U.S.C. § 371 national stage application of International Application No. PCT/US09/48419, filed Jun. 24, 2009, entitled "Treatment of Indications Using Electrical Stimulation," which is a continuation-in-part and claims priority to and the benefit of U.S. Non-provisional application Ser. No. 12/147,937, filed Jun. 27, 2008, entitled "Treatment of Indications Using Electrical Stimulation," the disclosure of which is incorporated herein by reference in its entirety.

BACKGROUND

The invention relates generally to medical devices and more particularly to devices and methods for use in electrical stimulation treatment.

Nerve cells consist of an axon for transmitting action potentials or neural impulses, and dendrites for receiving such impulses. Normally, nerves transmit action potentials from the impulse-sending axon of one nerve cell to the impulse-receiving dendrites of an adjacent nerve cell. At synapses, the axon secretes neurotransmitters to trigger the receptors on the next nerve cell's dendrites to initiate a new electrical current.

In some pathological states, transmission of action potentials is impaired, thus, activation of neural impulses is required to restore normal functioning. Electrically-excitable bodily tissues, such as nerves and muscles, may be activated by an electrical field applied between electrodes applied externally to the skin. Electric current flows through the skin between a cathodic electrode and an anodic electrode, eliciting action potentials in the nerves and muscles underlying the electrodes. This method is known for use in different types of stimulators, including transcutaneous electrical nerve stimulators (TENS), which relieve pain, therapeutic electrical stimulators, which activate muscles for exercise purposes, functional electrical stimulators which activate muscles for tasks of daily life, and stimulators that promote regeneration of damaged bones.

In other pathological states, action potentials are transmitted which do not serve a useful purpose; hence, blocking of unnecessary neural impulses is required to restore normal functioning. It has been reported that high-frequency stimulation can produce temporary reversible blocks of nerve axons. Generally, the frequency range is between 500 and 30,000 Hz.

Stimulation of nerves to either activate or block neural impulses is typically achieved with the use of an implanted stimulator (also known as a neural prosthesis or neuroprosthesis). Neural prostheses have been developed to restore hearing, to restore movement in paralyzed muscles, to modulate activity in nerves controlling urinary tract function and to suppress pain and tremor. In some cases, neural prostheses are designed to inhibit or suppress unwanted neural activity, for example to block pain sensation or tremors. However, all neural prostheses intended for long-term use require the implantation of a stimulator that contains electronic components and often a battery. In the case of pain and tremor suppression, the activated nerves reflexly inhibit the activity of neural circuits within the central nervous system. This indirect mode of reducing unwanted neural activity is sometimes called neuromodulation.

Surface electrical stimulators are used reflexly, for example, to reduce spastic hypertonus. A disadvantage of stimulation through electrodes attached to the body surface is that many non-targeted tissues may be co-activated along with the targeted tissues. This lack of selectivity often causes unwanted sensations and/or unwanted movements. Furthermore, tissues that lie deep within the body can be difficult or impossible to stimulate adequately, because most of the electrical current flowing between the electrodes flows through tissues closer to the electrodes than the targeted tissues. Selectivity may be improved by implanting insulated wires within the body that route electrical current from an implanted stimulator to the vicinity of the targeted tissues. This method is used, for example, in cardiac pacemakers, dorsal column stimulators, deep brain stimulators and sacral root stimulators. Cuffs containing the uninsulated ends of the wires may be placed around peripheral nerves to restrict most of the current to the vicinity of the nerve and limiting the spread of current to surrounding tissues, thereby improving selectivity. Implanted stimulators are expensive and often require a controller and/or power source external to the body. Batteries within the implanted stimulators need periodic replacement, entailing surgery.

In a minority of cases, stimulating wires are implanted in bodily tissues and led through the skin (percutaneously) to a connector located outside the body, to which an external stimulator is attached. External stimulators are typically less expensive than implanted stimulators, but the percutaneous wires provide a conduit for infection and therefore require daily cleaning and maintenance. This has generally limited the use of percutaneous electrodes to short-term applications. There is a need for a system which overcomes such problems and has the capability of activating or blocking nerve impulses depending upon the disorder to be treated. For example, a system and method is needed that can treat various indications such as: urinary incontinence through stimulation of the tibial nerve and/or the common peroneal nerve; headaches and/or facial pain through stimulation of a nerve related to the trigeminal nerve or a nerve adjacent to the upper cervical spine; in conjunction with a joint replacement procedure or prior to such a procedure; to promote wound healing; to treat a bone defect, such as, a fracture or a break; to reduce joint pain and/or arthritis pain; and/or to reduce or prevent muscle atrophy.

SUMMARY OF THE INVENTION

Systems and methods of treating a targeted body tissue (e.g., bone, soft tissue, muscle, ligaments, nerves, etc.) by stimulating the body tissue with an electric current are described herein. In one embodiment, a method includes implanting an implant entirely under the subject's skin. The implant includes a passive electrical conductor of sufficient length to extend from subcutaneous tissue located below either a surface cathodic electrode(s) or a surface anodic electrode(s) to the tibial nerve. The surface electrodes are positioned in spaced relationship on the subject's skin, with one of the electrodes positioned over the pick-up end of the electrical conductor such that the portion of the current is transmitted through the conductor to the tibial nerve, and such that the current flows through the tibial nerve and returns to the other of the surface cathodic electrode and the surface anodic electrode. An electrical current is applied between the surface cathodic electrode and the surface anodic electrode to cause the portion of the electrical current to flow through the implant to stimulate the tibial nerve. In some embodiments, a method includes electrical stimulation of a common peroneal nerve, stimulation of a nerve related to trigeminal nerve or a nerve adjacent to the upper cervical spine to treat headaches and/or facial pain, stimulation applied in conjunction with a joint replacement procedure or prior to such a procedure, stimulation to promote wound healing, stimulation to treat a bone defect, such as, a fracture or a break, stimulation to reduce joint pain and/or arthritis pain, and/or stimulation to reduce or prevent muscle atrophy.

BRIEF DESCRIPTION OF THE DRAWINGS

FIG. 2 illustrates the musculature and nervous system of a knee in extension.

FIG. 3 illustrates the musculature and nervous system of a knee in flexion.

DETAILED DESCRIPTION

Figure 1:
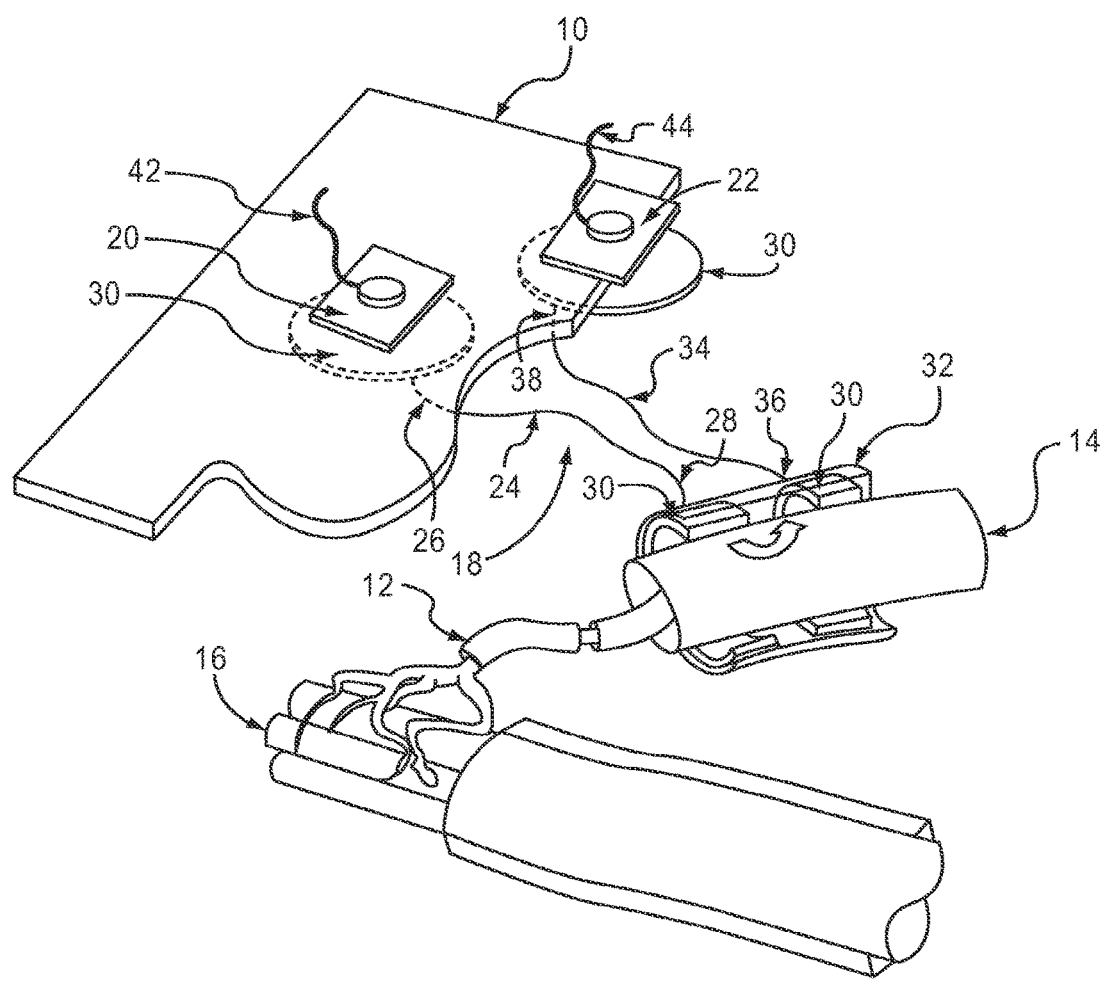
FIG. 1 is a schematic illustration of a three-dimensional view of an embodiment of the invention having an implanted electrical conductor, surface cathodic and anodic electrodes, and an implanted electrical return conductor.

Systems and methods are described herein that include the use of passive electrical conductors that can route electrical current to electrically stimulate a target body tissue. Such devices and methods can be used to either activate or block neural impulses, depending upon the frequency and the disorder to be treated.

A system as described herein can include, for example, an implant, a stimulator, such as an electric pulse generator, external electrodes, and a power source. An implant is provided for electrically stimulating a target body tissue in a subject to either activate or block neural impulses. Once implanted, the implant can provide a conductive pathway for at least a portion of the electrical current flowing between surface cathodic and anodic electrodes positioned in spaced relationship on a subject's skin, and transmits that portion of electrical current to the target body tissue to either activate or block neural impulses. Systems and methods incorporating such an implant are described herein.

As described herein, a "subject" can be, for example, an animal including a human. A body tissue can be, for example, a neural tissue (in the peripheral or central nervous system), a nerve, a muscle (skeletal, respiratory, or cardiac muscle) or an organ, for example, the brain, cochlea, optic nerve, heart, bladder, urethra, kidneys and bones.

The systems, methods and devices described herein can be used to treat various conditions in which stimulation to either activate or block neural impulses may be desired. Such conditions can include, for example, movement disorders (e.g., spasticity, hypertonus, rigidity, tremor and/or muscle weakness, Parkinson's disease, dystonia, cerebral palsy), muscular disorders (e.g., muscular dystrophy), incontinence (e.g., urinary bladder disorders), urinary retention, pain (e.g., migraine headaches, facial pain, neck and back pain, pain resulting from other medical conditions), epilepsy (e.g., generalized and partial seizure disorder), cerebrovascular disorders (e.g., strokes, aneurysms), sleep disorders (e.g., sleep apnea), autonomic disorders (e.g., gastrointestinal disorders, cardiovascular disorders), disorders of vision, hearing and balance, and neuropsychiatric disorders (e.g., depression). The systems, methods and devices can also be used for promoting bone growth (as required, for example, in the healing of a fracture), wound healing or tissue regeneration. The systems, methods and devices can also be used for inhibiting or reducing joint pain and/or arthritis pain.

The systems, methods and devices described herein can also be used, for example, in the prevention of muscle atrophy, venous thrombosis and joint stiffness due to long-term disability resulting from spinal cord injury, stroke, brain injury or neural disorder. The systems, methods and devices described herein can also be used in cases of acute or short term disabilities, resulting in immobilization, such as joint replacement or other surgeries, fractured bones, or a variety of other reasons. Some examples of such uses are described below.

Other treatment procedures and methods described herein include systems and methods for use in tibial nerve and/or common peroneal nerve stimulation in the treatment of urinary incontinence; for use in trigeminal nerve stimulation or stimulation of a nerve adjacent the cervical spine in the treatment of headaches and/or facial pain; for use in conjunction with joint replacement procedures; for use in applications to reduce joint and/or arthritis pain; and for use in applications to rehabilitate muscle attached to bone, such as in podiatry applications. In some embodiments, the systems and methods described herein are used to provide for movement of an immobile limb or body part. In some embodiments, systems and methods described herein can be used to increase blood flow through, for example, a limb, to reduce or eliminate muscle atrophy, and/or to improve muscle development. In some embodiments, an orthosis, such as a cast applied to a broken limb, can have a pulse generator (described in more detail below) embedded therein that can be used to apply an electrical current to an implant within the patient's body.

For stimulation of a target body tissue, particular frequencies to be applied depend upon many factors; for example, the type of nerve to be stimulated or blocked, the tissue which the nerve innervates, the size of the nerve, the subject to be treated, the type of condition, the severity of the condition, and the receptiveness of the subject to the treatment. In general, for blocking, high frequencies are useful, for example, the cyclical waveform can be applied at a frequency in the range of between 100 and 30,000 Hz, or alternatively in the range of between 100 and 20,000 Hz. Alternatively, the cyclical waveform can be applied at a frequency in the range of between 100 and 10,000 Hz, or in the range between 200 and 5,000 Hz. For stimulation or activation, low frequencies are generally used, for example, a frequency in the range of between 1 and 100 Hz, or alternatively, in the range of between 1 and 50 Hz. Alternatively, the frequency can be in the range of between 1 and 20 Hz. In some cases, the frequency can be in the range of between 1 and 150 Hz.

FIG. 1 is a schematic illustration of portions of a subject's body tissues, including skin 10, a nerve 12 with an overlying nerve sheath 14, and a muscle 16. FIG. 1 also illustrates an implant 18, a surface cathodic electrode 20 and a surface anodic electrode 22. The implant 18 is provided for electrically stimulating a target body tissue, such as a nerve 12, in a subject to either activate or block neural impulses. Once implanted, the implant 18 provides a conductive pathway for at least a portion of the electrical current flowing between the surface cathodic and anodic electrodes 20, 22.

When positioned in spaced relationship on the subject's skin 10, the surface cathodic and anodic electrodes 20, 22 make electrical contact with the skin 10 and transmit electrical current to the target body tissue. Surface cathodic and anodic electrodes 20, 22 can be selected from a conductive plate or sheet, a conductive gel electrode, a conductive rubber or polymer electrode that may be partially coated with an electrode paste or gel, or a moistened absorbent pad electrode. For example, self-adhesive hydrogel electrodes of the type used to stimulate muscles, with surface areas, for example, of 5 square centimeter, can be used. In some embodiments, electrodes having larger or smaller surface areas can alternatively be used. Platinum iridium electrodes, which are composed typically of 80% or more platinum and 20% or less iridium, can also be used (for example, 85% platinum-15% iridium alloy; 90% platinum-10% iridium alloy). The positions of the surface cathodic and anodic electrodes 20, 22 on the skin 10 may vary, depending upon the location and nature of the target body tissue.

The implant 18 includes a passive electrical conductor 24 of sufficient length to extend, once implanted, from subcutaneous tissue located below the surface cathodic electrode 20 to the target body tissue, for example nerve 12. The electrical conductor 24 can be formed from a metal wire, carbon fibers, a conductive rubber or other conductive polymer, or a conductive salt solution in rubber. Multistranded, TEFLON-insulated, stainless-steel wire conductors of the type used in cardiac pacemaker leads can also be used. MP35N alloy (a nonmagnetic, nickel-cobalt-chromium-molybdenum alloy) which is commonly used in parts for medical applications is also suitable. The electrical conductor 24 has a pick-up end 26 and a stimulating end 28, and is insulated between the pick-up end 26 and the stimulating end 28.

The electrical impedance of the interface between the pick up end 26 and the stimulating end 28 of the conductor 24 (when implanted) and the surrounding body tissue may be reduced by enlarging the surface area of the ends 26, 28. For that purpose, one or both of the pick-up end 26 and the stimulating end 28 form electrical terminations 30 having sufficient surface area for reducing the electrical impedance of the interface between the pick-up end 26 and the stimulating end 28 of the electrical conductor 24 and the surrounding body tissues. The pick-up end 26 forms an electrical termination 30 which has a sufficient surface area to allow a sufficient portion of the electrical current to flow through the electrical conductor 24, rather than flowing through body tissue between the surface cathodic electrode 20 and the surface anodic electrode 22, such that the target body tissue is stimulated to either activate or block neural impulses. The stimulating end 28 also forms an electrical termination 30 for delivering the portion of electrical current to the target body tissue (i.e., nerve 12).

Terminations 30 have sufficient surface area for providing high conductivity contact with body tissues, and lowering the electrical impedance between the body tissue and the conductor 24. If the surface area is minimal, the amount of current flowing through a conductor to the termination is reduced to an ineffective amount. The surface area required can be determined by a knowledge of the electrical impedance of the interface between the tissue and the terminations 30 at the receiving or pick-up end 26 and the stimulating end 28. Beneficial results have been obtained by making the surface area of metal terminations 30 at the ends 26, 28, for example, about 0.5 $cm^2$. The terminations 30 at the ends 26, 28 can alternatively have a larger or smaller surface area. The electrical impedance of each interface between tissue and terminations 30 at ends 26, 28 can be about 5 times the electrical impedance of all the subcutaneous tissue between surface electrodes 20, 22. For example, a typical value of tissue impedance is 200 ohms. The impedance of the conductor 24 can be chosen to be very small, for example, 5 ohms. In such a case, the sum of the two interface impedances of the terminations 30 plus the conductor impedance can be about 2000 ohms, or ten times the tissue impedance. Thus, about 10% of the current applied between surface electrodes 20, 22 flows through conductor 24 to the target tissue. In the case of the target tissue being a nerve 12 supplying a muscle 16, the amount of current between surface electrodes 20, 22 required to produce a useful muscle contraction of the target muscle 16 remains below the threshold level of activation of nerve endings in the subcutaneous tissue immediately between surface electrodes 20, 22. This is a beneficial relationship, because it means that target muscles 16 can be activated with little or no local sensation or local muscle contractions under the surface electrodes 20, 22.

Terminations 30 of various shapes, materials and spatial arrangements can be used; for example, terminations 30 can provide an enlarged surface in the form of a coil, spiral, cuff, rod, or a plate or sheet in the form of an oval or polygon. As an example, FIG. 1 illustrates a termination 30 as a plate or sheet in the form of an oval at the pick-up end 26 of the electrical conductor 24, and in the form of a cuff at the stimulating end 28. The cuff or a portion thereof can encircle or partially encircle the entirety or part of the nerve sheath 14 of the nerve 12. The cuff or a portion thereof can be positioned proximate to the nerve sheath 14, or the inner surface of the cuff or a portion thereof can directly contact the nerve sheath 14.

Beneficial results can be obtained with stainless-steel plates or sheets in the form of an oval that is about 0.5 cm$^2$ in surface area and 1 mm thick, or made, for example, of metal foil and stainless-steel mesh and being about 0.5 cm$^2$ in surface area and 0.3 mm thick. For terminations 30 of conductors in the form of a nerve cuff, nerve cuffs made, for example, of metal foil or stainless-steel mesh and being 0.5 to 1 cm$^2$ in surface area and 0.3 mm thick can be used. Further, silastic elastomer cuffs, for example, ranging from 5 mm to 15 mm in length, having a 4 mm to 6 mm inside diameter, and that are 1 mm thick are also suitable.

In some embodiments, terminations 30 can be formed from uninsulated ends 26, 28 of the electrical conductor 24, or from other conductive or capacitive materials. In some embodiments, the terminations 30 can include an electrode. Terminations 30 can be formed by coiling, spiraling or weaving long, uninsulated lengths of the pick-up or stimulating ends 26, 28 to provide a sufficient surface. The surface area of the termination is thus "enlarged" relative to the surface area of a shorter length of the electrical conductor 24. This raises the effective surface area of the terminations 30 within a small space to provide higher conductivity contact with body tissues, and to lower the electrical impedance between the body tissue and the conductor 24 to allow current flow in the conductor 24 in preference to in the body tissue. Sufficient current flow is thereby provided in the conductor 24 to stimulate the target tissue. Alternatively, prefabricated terminations 30 (for example, plates or sheets in the form of ovals or polygons) can be attached directly to the pick-up end 26 and/or stimulating end 28. Further, terminations 30 can be coated or modified with conductive materials to maximize the flow of electrical current through the target body tissue.

The spatial arrangement of the terminations 30 can be varied; for example, multiple terminations 30 can also be applied to different parts of a body tissue. In some embodiments, the terminations 30 can be in the form of closely-spaced contacts enclosed within an embracing cuff 32 placed around the nerve 12. The embracing cuff 32 can be formed, for example, with conductive silicone rubber.

Electrical impedance can be further reduced by providing conductive or capacitive coatings, or an oxide layer on the terminations 30. The coating can be selected from a material whose structural or electrical properties improve the electrical conductance between the tissue and the conductor, for example, by providing a complex surface into which tissue can grow (for example, a polymer such as poly-diethoxy-thiophene, or suitable oxide layers including tantalum and sintered iridium). In addition, the terminations 30 can have coatings which provide an anti-inflammatory, anti-bacterial or tissue in-growth effect. The coating can be, for example, a substance selected from an anti-inflammatory agent, anti-bacterial agent, antibiotic, or a tissue in-growth promoter.

In some embodiments, a second implant including an electrical return conductor 34 can be included with the implant 18, as shown in FIG. 1. The electrical return conductor 34 can be sufficient length to extend from the target body tissue to subcutaneous tissue located below the surface anodic electrode 22. The electrical return conductor 34 provides a low-impedance conductive pathway from the target body tissue to the surface anodic electrode 22, thereby concentrating the electric field through the target tissue. The electrical return conductor 34 can be formed, for example, from a metal wire, carbon fibers, a conductive rubber or other conductive polymer, or a conductive salt solution in rubber. The electrical return conductor 34 has a collecting end 36 and a returning end 38, and is insulated between its ends 36, 38. Both the collecting end 36 and the returning end 38 form electrical terminations 30 (as described above for conductor 24) for reducing the electrical impedance of the interface between the collecting end 36 and returning end 38 of the electrical return conductor 34 and the surrounding body tissues. The collecting end 36 forms an electrical termination 30 (shown in FIG. 1 in the form of a cuff), which has a sufficient surface area to allow a portion of the electrical current delivered to the target body tissue to return through the electrical return conductor 34 in preference to returning through body tissue. The returning end 38 forms an electrical termination 30 (shown in FIG. 1 as a plate or sheet in the form of an oval), which returns the electrical current to the surface anodic electrode 22 via the subcutaneous tissue and skin underlying the surface anodic electrode 22.

Multiple surface electrodes 20, 22 can be fabricated on a single non-conductive substrate to form an electrode array that may be conveniently attached to the skin 10. Similarly, multiple terminations 30 of implanted conductors 24 can be fabricated on a substrate to form an array. By matching the physical layout of the surface electrode array to that of the implanted terminations array, a good spatial correspondence of surface and implanted conductors may be achieved in a convenient and reproducible manner. Surface electrode arrays in which the conductivity of each element of the array may be independently controlled could also be used to adjust the conductivity between the surface electrodes and the terminations in an implanted array.

A power source (not shown) can be used to provide operating power to a stimulator (not shown), which is disposed external to the subject's body. The stimulator can be electrically connected to the surface cathodic and anodic electrodes 20, 22 via electrical wires or conductors 42 and 44, to supply electrical current to the surface cathodic and anodic electrodes 20, 22. The current can be resistive or capacitive, depending on the net impedance encountered between the electrodes 20, 22.

The stimulator can be, for example, a pulse generator. Examples of stimulators are described in U.S. Patent Publication No. 2006/0184211 ("the '211 publication"), the disclosure of which is hereby incorporated by reference in its entirety. The use of a pulse generator and various examples applications are also described in the '211 publication. In general, a flow of electrical current from the power source 40 can be supplied into the skin 10 via a cathodic wire 42 at the surface cathodic electrode 20, and via an anodic wire 44 at the surface anodic electrode 22. Power can be provided to the stimulator either through a wire connection or through a wireless connection, via a wireless energy source, such as, radiofrequency (RF).

Although most of the electrical current flows through the body tissues in proximity to the surface cathodic and anodic electrodes 20, 22, there is also flow of electrical current through the electrical conductor 24, nerve 12, and electrical return conductor 34. As shown in FIG. 1, the surface cathodic electrode 20 is positioned over the pick-up end 26 of the electrical conductor 24, so that a portion of the current is transmitted through the conductor 24 to the target body tissue, and current flows through the target body tissue and returns to the anodic surface electrode 22 through body tissues. This can also be achieved through the implanted electrical return conductor 34 extending between the target body tissue and subcutaneous tissue located below the surface anodic electrode 22.

The complete electrical path of the portion of the electrical current is as follows: cathodic wire 42, surface cathodic electrode 20, skin 10, termination 30, pick-up end 26, electrical conductor 24, stimulating end 28, termination 30, nerve sheath 14, nerve 12, termination 30, collecting end 36, electrical return conductor 34, returning end 38, termination 30, skin 10, surface anodic electrode 22 and anodic wire 44. The pulses of electrical current can elicit action potentials which are conducted along nerve 12 to muscle 16, causing it to contract. Alternatively, electrical current in the form of high frequency waveforms can block action potentials conducted along nerve 12 to muscle 16 to prevent muscle contractions.

Various disorders are amenable to treatment using an implant, such as implant 18, shown in FIG. 1. As described below and in the '211 publication incorporated herein, the implanted passive electrical conductors are capable of routing electrical current to stimulate various target body tissues to either activate or block neural impulses depending upon the frequency and disorder to be treated.

In one example procedure, a stimulation system can be used in conjunction with a joint replacement procedure (for example, knee replacement or hip replacement) to condition the muscles before the surgery, reduce the post-procedure pain, enhance the post-operative recovery and/or reduce or prevent some of the side effects associated with a joint replacement procedure.

Joint replacement is a common operation used in modern orthopaedic surgery. It includes the replacement of painful, arthritic, worn or cancerous parts of a joint with artificial surfaces shaped in such a way as to allow joint movement. Although not always accomplished, many joint replacement procedures result in a full recovery of range of motion. Because joint replacement is a major surgery, an extensive pre-operative activity is typically required. This activity includes selection of implant design and size by matching x-ray images. Early mobilization of the patient is thought to be a key to reducing the chances of complications, such as venous thromboembolism and Pneumonia. It is common practice to try to mobilize a patient as soon as possible after surgery and to ambulate with walking aids when tolerated. Depending on the joint involved, and the pre-op status of the patient, the time of hospitalization can vary, for example, from 1 day to 2 weeks, with an average being 4-7 days.

Physiotherapy is also used extensively to help patients recover function after joint replacement surgery. A graded exercise program can be used. Initially, the patients' muscles have not healed after the surgery; exercises for range of motion of the joints and ambulation should not be strenuous. Later when the muscle is healed the aim of exercise expands to include strengthening and recovery of function.

The stress of a surgical operation may result in medical problems of varying incidence and severity, like heart attack, stroke, venous thromboembolism, pneumonia, increased confusion, and urinary tract infection (UTI). Intra-operative risks include mal-position of the components, shortening, instability/dislocation, loss of range of motion, fracture of the adjacent bone, nerve damage, or damage to blood vessels. Some immediate risks include deep or superficial infection and dislocation. Some medium-term risks include dislocation, persistent pain, loss of range of motion, weakness, indolent infection. Long-term risks can include loosening of the components due to fatigue and/or wear of the bearing surfaces. As a result, the component may move inside the bone resulting in pain. Fragments of wear debris may also cause an inflammatory reaction with bone absorption which can cause loosening.

Knee replacement, or knee arthroplasty, is a common procedure performed to relieve the pain and disability from degenerative arthritis, most commonly osteoarthritis, but other arthritides as well. Such procedures include replacing the diseased and painful joint surfaces of the knee with metal and plastic components that are shaped to allow continued motion of the knee. A total knee replacement (TKR) may be performed to treat incapacitating pain from arthritis of the knee that may affect such activities as walking and/or standing. A TKR surgery involves exposure of the front of the knee, with detachment of part of the quadriceps muscle (vastus medialis) from the patella. Minimally invasive surgery is being developed in TKR, but has not yet found complete acceptance. The goal is to spare the patient a large cut in the quadriceps muscle which could increase postoperative pain or lengthen disability.

A unicompartmental arthroplasty (UKA), also called partial knee replacement, is an option for some patients. In such a procedure, the knee is generally divided into three "compartments": medial (the inside part of the knee), lateral (the outside), and patellofemoral (the joint between the kneecap and the thighbone). Most patients with arthritis severe enough to consider knee replacement have significant wear in two or more of these compartments and are best treated with total knee replacement. A minority of patients (for example, 10-30%) have wear confined primarily to one compartment, usually the medial, and may be candidates for unicompartmental knee replacement. Advantages of UKA, as compared to TKR, include smaller incision, easier post-op rehabilitation, shorter hospital stay, less blood loss, lower risk of infection, stiffness, and blood clots, and easier revision if necessary. Lupus, Psoriatic, or marked deformity may not be candidates for a UKA procedure.

Post-operative rehabilitation usually includes the use of protected weight bearing on crutches or a walker until the quadriceps muscle has healed and recovered its strength. Continuous passive motion (CPM) is also commonly used. Post operative hospitalization can vary, for example, from one day to seven days on average depending on the health status of the patient and the amount of support available outside the hospital setting. Usually full range of motion is recovered over the first two weeks. At six weeks, patients typically have progressed to full weight bearing with a cane. Complete recovery from the operation involving return to full normal function can take, for example, three months, and some patients notice a gradual improvement lasting many months longer than that.

There are risks and complications that accompany TKR or UKA procedures. For example, blood clots in the leg veins are the most common complication of knee replacement surgery. Periprosthetic fractures are also becoming more frequent with aging patients and can occur intraoperatively or postoperatively. The knee at times may not recover its normal range of motion (e.g., 0-135 degrees) after total knee replacement. Some patients can achieve 0-110 degrees of motion, but in some cases stiffness of the joint can occur. In some situations, manipulation of the knee under anesthetic is used to improve post operative stiffness. In some patients, the kneecap is unstable post-surgery and dislocates to the outer side of the knee. This can be painful and may require surgery to realign the kneecap. Knee replacement implants can last up to, for example, 20 years in many patients, and this can depend, for example, on how active the patient is after surgery.

Hip replacement, also referred to as hip arthroplasty, is a surgical procedure in which the hip joint is replaced by a prosthetic implant. Such joint replacement orthopaedic surgery generally is conducted to relieve arthritis pain or fix severe physical joint damage as part of the hip fracture treatment. Some hip replacement patients can suffer chronic pain after the surgery. Because such side effects are usually not detectable with X-ray or MRI, it can be difficult to determine the source of such pain. Generally, it is believed that such pain is caused by nerve damage during the replacement surgery.

As an alternative to seeking a joint replacement, such as hip and knee replacement described above, the use of electrical stimulation can delay or defer the need for such joint replacement surgery. For example, a pulsed electrical stimulation device can be used to defer total knee replacement surgery. In some cases, the use of electrical stimulation, can potentially reduce joint pain and arthritis pain significantly, thereby, eliminating the need for any joint replacement surgery.

Following a TKR procedure, patients can exhibit long-term weakness of the quadriceps and diminished functional capacity compared to age-matched healthy controls. The pain and swelling resulting from surgery may contribute to quadriceps weakness. Electrical stimulation can also be used to enhance recovery after a joint replacement procedure. For example, neuromuscular electrical stimulation (NMES) can be added to a voluntary exercise program to improve quadriceps muscle strength. The application of electrical stimulation during recovery from TKR can also effectively reduce extensor lag and decrease the length of the hospital stay.

Thus, a stimulation system as described herein and in the '211 publication can be used in conjunction with joint replacement. As described above, a portion of the electrical stimulation delivered transcutaneously by the external stimulator (e.g., pulse generator) is picked up by the pick-up end (e.g., 26) of the implanted conductor (e.g., conductor 24) and is delivered to the stimulating end (e.g., 28) of the conductor, which is located near the targeted stimulating location. For example, the stimulating end can be positioned in proximity to a joint, such as a hip or knee joint, or it may be positioned near the motor point(s) activating the muscles associated with the joint.

With a stimulation system as described herein as compared with a transcutaneous device, the stimulation may be delivered to the specific location (e.g. to the specific nerve) with no unpleasant sensation from cutaneous receptors due to delivery of the stimulation thru the skin and with no risk of activating non-targeted areas (as in TENS). In addition, as compared with percutaneous stimulation, the risk of inflammation or contamination due to the lead protruding thru the skin can be reduced or eliminated using a stimulation system as described herein. As compared to full size implantable stimulators, only a minimally invasive procedure is required with the stimulation system described herein. A stimulation system as described herein is usually also not associated with tunneling the leads from the targeted stimulation location to the place available for implantation of the stimulator (under-skin pocket), which may be relatively far away. For example, stimulating the arm may require tunneling the leads from the arm to the chest, where the stimulator will be implanted. In addition to the invasiveness of such a procedure, there is a risk of lead migration or lead damage associated with the long leads crossing the joints.

A stimulation system as described herein used in conjunction with a joint replacement procedure can be used to achieve a variety of different benefits. For example, use of stimulation can delay or defer the need for a joint replacement procedure. Conditioning of the muscles/joint can be done before a replacement procedure (e.g. increasing range of motion). Stimulation of a joint can also improve recovery after a joint replacement procedure. For example, improvements can be made in pain management and/or in management of muscle performance. In some cases, stimulation of a joint can also help prevent deep venous thrombosis. In some cases, stimulation of a joint can eliminate the need for such a joint replacement procedure. For example, such stimulation can significantly reduce joint and/or arthritis pain such that joint replacement is no longer needed.

For example, to improve range of motion or muscle condition related to a knee replacement procedure, knee extensors and/or knee flexors can be stimulated using a stimulation system as described herein. In this example, knee extension is performed by Quadriceps Femoris muscle (which include Sartorius, Vastus intermedius, Vastus Lateralis and Vastus medialis), innervated by the Femoral nerve), as shown FIG. 2. Knee flexion can be performed by the Hamstring (Lateral Hamstring and Medial Hamstring), controlled by the Sciatic nerve and Tibial nerve, as shown in FIG. 3.

To cause motor point stimulation, a stimulation system including an implant (e.g., implant 18) can be implanted near the subject nerves. The stimulation frequency can be, for example, lower than 50 Hz. A single implant can be used, for example, causing knee extension, and it can be operated cyclically. For example, stimulus can be applied every 30 seconds for 5 seconds. The knee will be extended during the stimulation, and will be relaxed to its original position (by gravity) during the rest of the cycle. It is also possible to use two or more implants. For example, one implant to cause knee extension and the other to cause knee flexion. In this case, the implants can be operated synchronously, for example, a cycle of 5 seconds stimulating the extension, 10 seconds pause, 5 seconds stimulating flexors, 10 seconds pause, etc. When using a higher frequency of stimulation (e.g., above 30 Hz), pain relief can be achieved, which may be helpful at any of multiple stages of a knee replacement procedure.

In another example application, a stimulation system as described herein can be used to treat urinary incontinence by applying electrical stimulation to the common peroneal (CP) nerve (e.g., common fibular nerve; external popliteal nerve; peroneal nerve), and/or the tibial nerve. FIGS. 4-8 illustrate applications of various configurations of a implant with the cathodic electrode(s) and anodic electrode(s) positioned at various locations on a feline F. A schematic illustration of a feline subject is illustrated in FIGS. 4-8.

Figure 4:
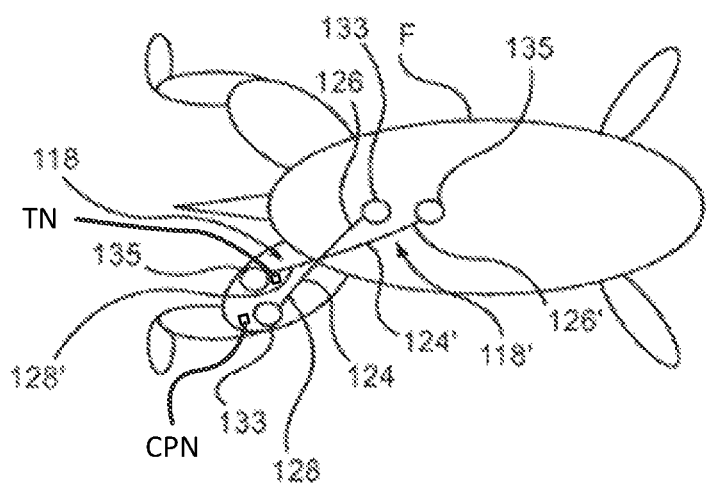
FIG. 4 is a top view of a schematic illustration of an implant according to an embodiment disposed within a schematic illustration of a feline.

FIG. 4 illustrates the feline F with two implants implanted under the skin of the feline F. A first implant 118 includes a passive conductor 124 having a pick-up end 126 and a stimulating or delivery end 128 and terminations 133. The delivery end 128 is disposed in proximity to a common peroneal nerve (a portion of which is represented by the box labeled CPN shown in FIG. 4) of the feline F. A second implant 118' includes a passive conductor 124' having a pick-up end 126' and a stimulating or delivery end 128', and terminations 135. The delivery end 128' is disposed in proximity of a tibial nerve (a portion of which is represented by the box labeled TN shown in FIG. 4) of the feline F. FIGS. 5-8 do not show the implants 118 and 118' disposed under the skin of the feline F for purposes of illustration. Reference to the implants 118 and 118' in the below description refer to FIG. 4.

Figure 5:
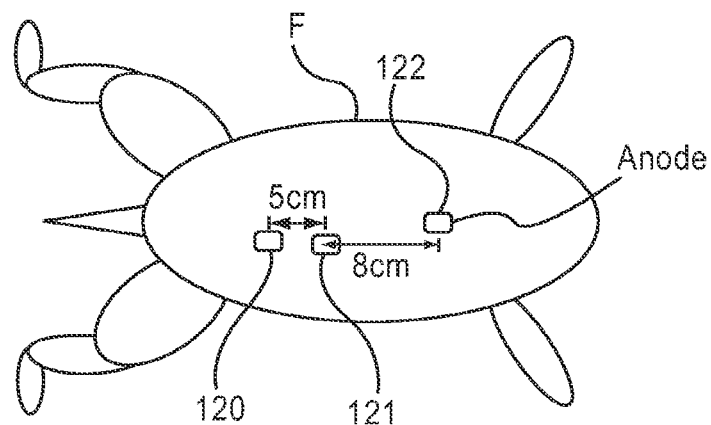
FIG. 5 is a top view of a schematic illustration of a portion of a system according to an embodiment disposed within the schematic illustration of a feline of FIG. 4 illustrating a first configuration.

FIG. 5 illustrates a stimulation system attached to the feline F with the implants 118 and 118' implanted within the feline F. A first cathodic electrode 120 is attached to the external surface of the feline F over the pick-up end 126 of a the conductor 124 and a second cathodic electrode 121 is attached to the surface of the feline F over the pick-up end 126' of the conductor 124'. In this example, an electrical current is applied to the first cathodic electrode 120 and the second cathodic electrode 121 (e.g., via a pulse generator), and a portion of the electrical current is picked up by the pick-up ends 126, 126' of the conductors 124, 124', passed through the conductors 124, 124' to the stimulating ends 128, 128' of the conductors 124, 124' in proximity of the CP nerve and the tibial nerve, respectively. Thus, this example provides cathodic stimulation. In this example, a single anodic electrode 122 is positioned 8 cm from the cathodic electrode 121 and 5 cm from the cathodic electrode 120.

Figure 6:
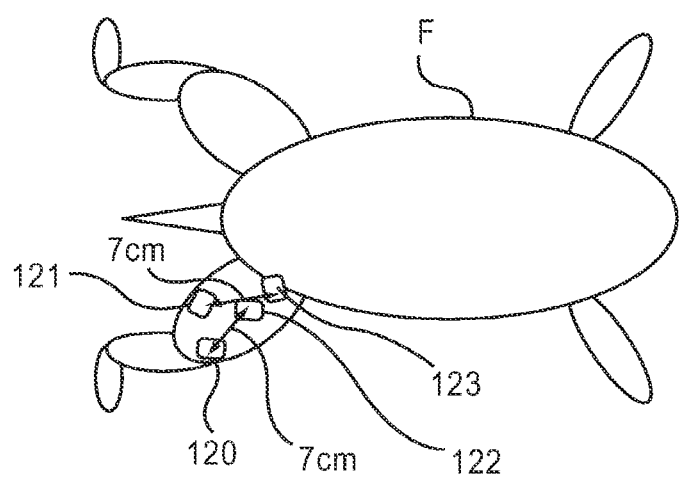
FIG. 6 is a top view of a schematic illustration of a portion of a system according to an embodiment disposed within the schematic illustration of a feline of FIG. 4 illustrating a second configuration.

FIG. 6 illustrates a system having cathodic electrodes over the delivery terminals (e.g., stimulating ends of the implants) in the proximity of the nerves to be treated, and anodic electrodes over the pick-up terminals of the implants. In this embodiment, a first cathodic electrode 120 is attached to the feline F over the delivery end 128 of the implant 118 in the proximity of the CP nerve, and a second cathodic electrode 121 is attached to the feline F over the delivery end 128' of the implant 118' in the proximity of the tibial nerve. A first anodic electrode 122 is attached to the feline F at 7 cm from the first cathodic electrode 120, and a second anodic electrode 123 is attached to the feline F at 7 cm from the second cathodic electrode 121. In this embodiment, electrical current is provided and a portion of the electrical current is picked up by the pick-up ends 126, 126' of the conductors 124, 124', passed through the conductors 124, 124' to the stimulating ends 128, 128' of the implants 118, 118' over which the cathodic electrodes 120, 121 are disposed.

Figure 7:
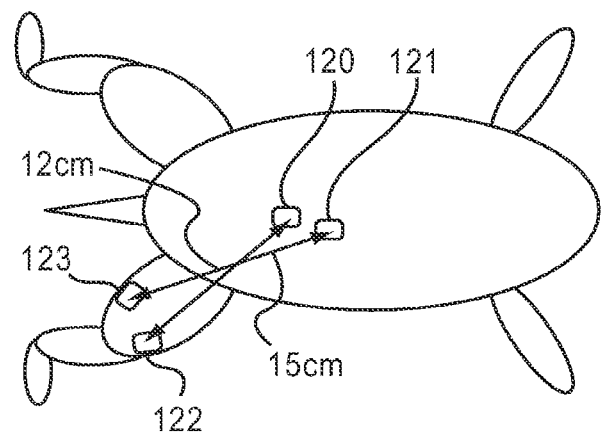
FIG. 7 is a top view of a schematic illustration of a portion of a system according to an embodiment disposed within the schematic illustration of a feline of FIG. 4 illustrating a third configuration.

FIG. 7 illustrates a system having a cathodic pick-up and an anodic delivery configuration. In this embodiment, a first cathodic electrode 120 is attached to the feline F over the pick-up end 126 of the implant 118, and a second cathodic electrode 121 is attached to the feline F over the pick-up end 126' of the implant 118'. A first anodic electrode 122 is attached to the feline F over the delivery end 128 of the implant 118 in the proximity of the CP nerve, and a second anodic electrode 123 is attached to the feline F over the delivery end 128' of the implant 118' in the proximity of the tibial nerve. In this embodiment, the first cathodic electrode 120 is positioned 12 cm from the first anodic electrode 122, and the second cathodic electrode 121 is positioned 15 cm from the second anodic electrode 123. Electrical current is provided to the cathodic electrodes 120, 121 and a portion of the electrical current is picked up by the pick-up ends 126, 126' of the conductors 124, 124', passed through the conductors 124, 124' to the delivery ends 128, 128' over which the anodic electrodes 122, 123 are disposed.

Figure 8:
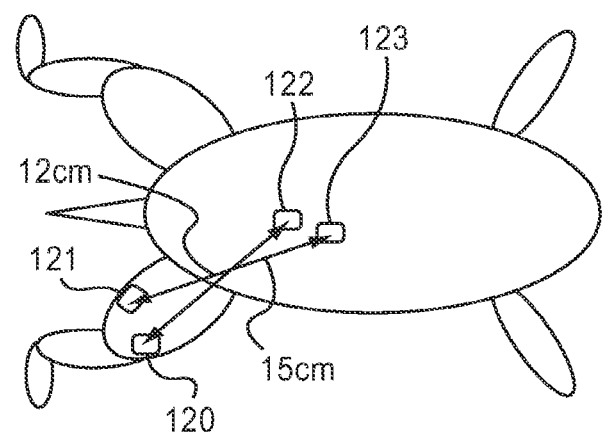
FIG. 8 is a top view of a schematic illustration of a portion of a system according to an embodiment disposed within the schematic illustration of a feline of FIG. 4 illustrating a fourth configuration.

FIG. 8 is an example of a system having the cathodic electrodes over the delivery terminals and the anodic electrodes over the pick-up terminals. In this configuration, a first cathodic electrode 120 is placed over the delivery end 128 of the implant 118 in the proximity of a CP nerve, and a second cathodic electrode 121 is placed over the delivery end 128' of the implant 118' in the proximity of the tibial nerve. A first anodic electrode 122 is placed over the pick-up end 126 of the implant 118 and a second anodic electrode 123 is placed over the pick-up end 126' of the implant 118'. As with the embodiment of FIG. 7, the first cathodic 120 is positioned 12 cm from the first anodic electrode 122, and the second cathodic electrode 121 is positioned 15 cm from the second anodic electrode 123. In this embodiment, electrical current is provided to the anodic electrodes 122, 123, a portion of the electrical current is picked up by the pick-up ends 126, 126' of the conductors 124, 124', passed through the conductors 124, 124', to the delivery ends 128, 128' over which the cathodic electrodes 120, 121 are disposed. Thus, this configuration is an example of anodic stimulation.

Figure 9:
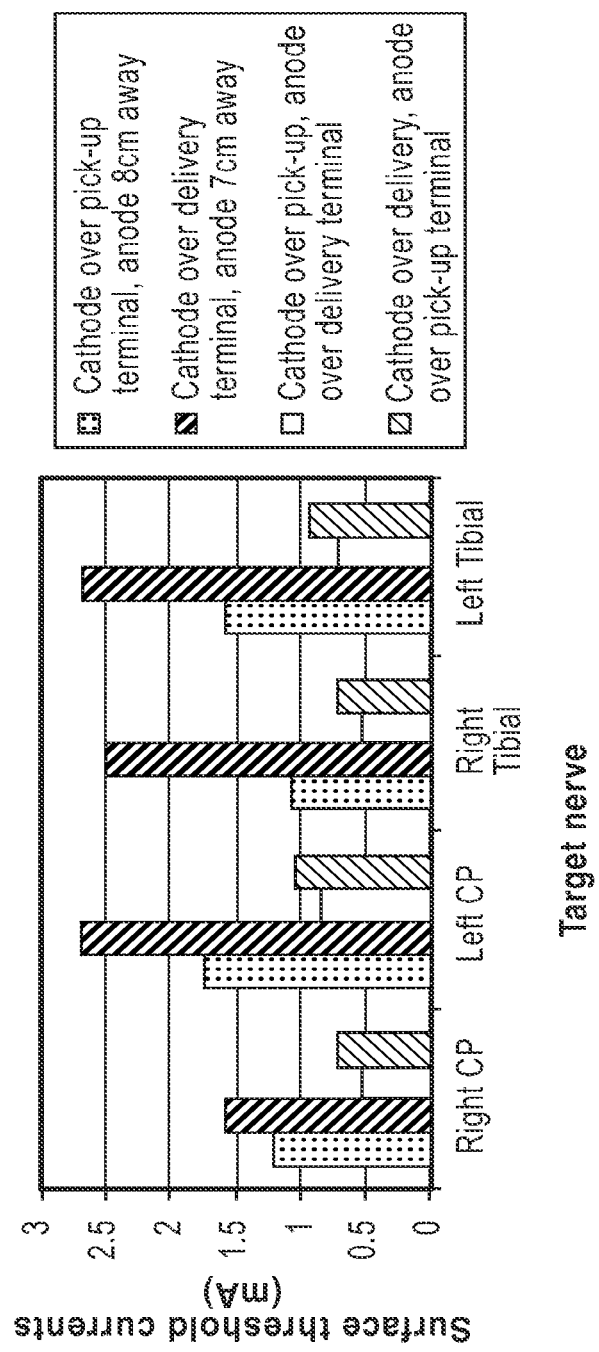
FIG. 9 is a graph illustrating the surface threshold currents associated with each of the configurations of the system of FIGS. 5-8.

For each of the illustrated configurations in FIGS. 5-8, a surface threshold current can be determined. FIG. 9 is a graph illustrating an example of the threshold currents associated with each configuration when a cuff-style implant was implanted within the feline F. As shown in FIG. 9, when external electrodes are placed over both the pick-up ends and the stimulating ends of the conductors (as shown in FIGS. 7 and 8), only half the threshold is required than for the configuration where there is no external electrode placed over the pick-up end of the conductor (FIG. 5).

In another example application, an implant described herein can be used to rehabilitate muscle attached to bone, such as in podiatry applications. An implant can also be used to provide assistance to movement of immobile limbs, such as a paralyzed hand. Such electrical stimulation is described in U.S. Pat. No. 6,961,623 ("the '623 patent") the disclosure of which is hereby incorporated herein by reference in its entirety. For example, the '623 patent describes an apparatus and method for controlling a device or process with vibrations produced through clicking together of a patient's teeth. Such a device can be used to actuate a stimulator (e.g., pulse generator) in a stimulation system as described herein.

Other applications for which a system and implant as described herein can be used include increasing blood flow, for example, within a limb, and/or to increase the speed of recovery of wounds. Chronic wounds, including venous ulcers, diabetic foot ulcers and pressure sores, can be a major public health problem. The total prevalence of such wounds in the United States has been estimated to range from 3 to 6 million. Difficult to heal wounds may lead to high rates of morbidity and mortality, and negative effects on quality of life. While leg and foot ulcers have numerous causes, such as venous disease, arterial disease, mixed venous-arterial disease, diabetic neuropathy, trauma, immobility, and vasculitis, over 90% of chronic lesions are related to venous disease, arterial disease, and neuropathy. Chronic wounds may require intervention to promote healing and to prevent infection, progression, and recurrence. Regardless of the cause, ulcer treatment usually begins with conservative therapies such as pressure relief, sterile dressings, and topical antibiotics. If conservative treatments fail to promote wound healing, surgical treatments such as sclerotherapy of the affected vein, skin flap reconstruction, or amputation of a digit or foot may be necessary. A less invasive approach to management of chronic wounds involves electrical stimulation.

When skin is damaged, not only are epithelial cells sometimes destroyed, but a large quantity of collagen can also be lost. This is important because collagen makes up approximately 75% of the weight of the skin. To stimulate skin healing, a variety of methods have been used, such as, for example, the topical application of herbal remedies like Aloe Vera extract, the use of soft laser, natural honey, electromagnetic pulses and fibroblast growth factor. Even though good results have been achieved by these methods, the customary approach remains the prevention of infection using antibacterial and antiseptic agents, and sometimes hygroscopic powders. However, these approaches may be of limited benefit if an adequate blood supply to the affected area is not promoted especially in severe cases such as extensive burn injuries, diabetic ulcers, ischemic flaps, necrotic wounds and large areas of skin.

Thus, stimulating wound healing using electricity can be done using an implant as described herein. In addition, numerous morphological and functional effects of electric stimulation have been identified, both at the cellular and at the tissue level.

As described above, electrical stimulation refers to the application of an electrical current through electrodes placed directly onto the skin in close proximity of the wound. Electrical stimulation as a technique to promote wound healing may: 1) increase ATP concentration in the skin, 2) increase DNA synthesis, 3) attract epithelial cells and fibroblasts to wound sites, 4) accelerate recovery of damaged neural tissue, 5) reduce edema, 6) increase blood flow, and/or 7) inhibit pathogenesis.

Similar to the other above-described applications of a stimulation system and implant, electrical stimulation (ES) in wound care involves the placement of electrodes in direct contact, or in close proximity to a skin wound, thereby creating an electrical current that passes through the wound. The skin possesses an electrical field, and the presence of a wound can disrupt this electrical field. The use of ES as an adjunctive treatment for wound healing can help repair the electrical field of the skin. There are several modalities of ES used in the treatment of chronic wounds. In one example, low intensity direct current (LIDC) can be applied, which involves application of direct current of low intensity, typically between 100 µA and 1 mA. In another example, low intensity pulsed current (LIPC) can be applied, which involves application of a pulsed direct current of about 10 mA, with a pulse repetition of the order of 100 pulses per second. In another example, high voltage pulsed current (HVPC) can be applied, which includes the application of a pulsed direct current of high voltage. The pulses, can be, for example, twin pulses of short duration, between 100 and 500 V.

Figure 10:
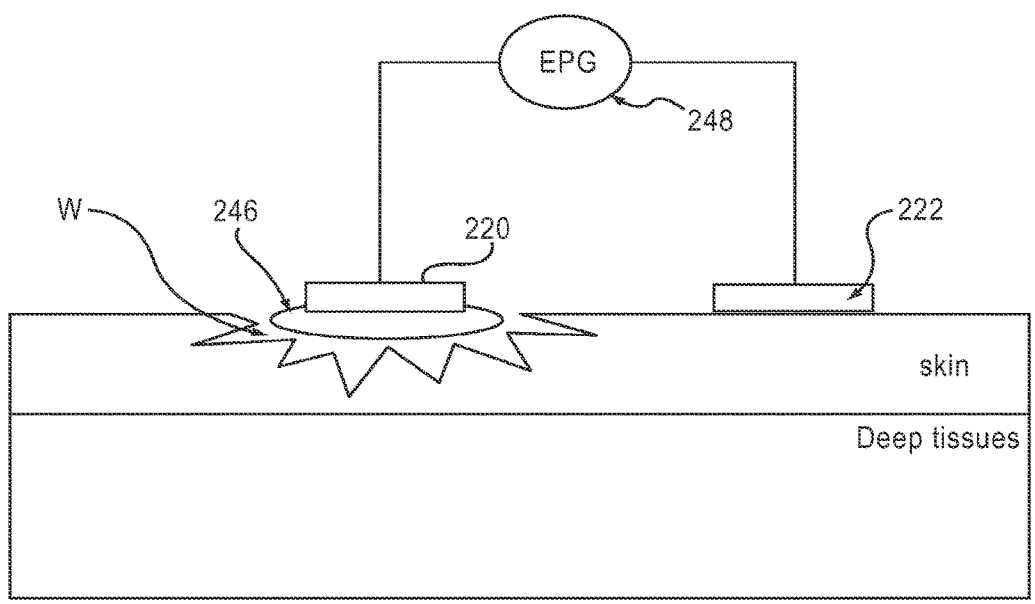
FIG. 10 is a side view of a schematic illustration of a system illustrating an application to treat a wound.
Figure 11:
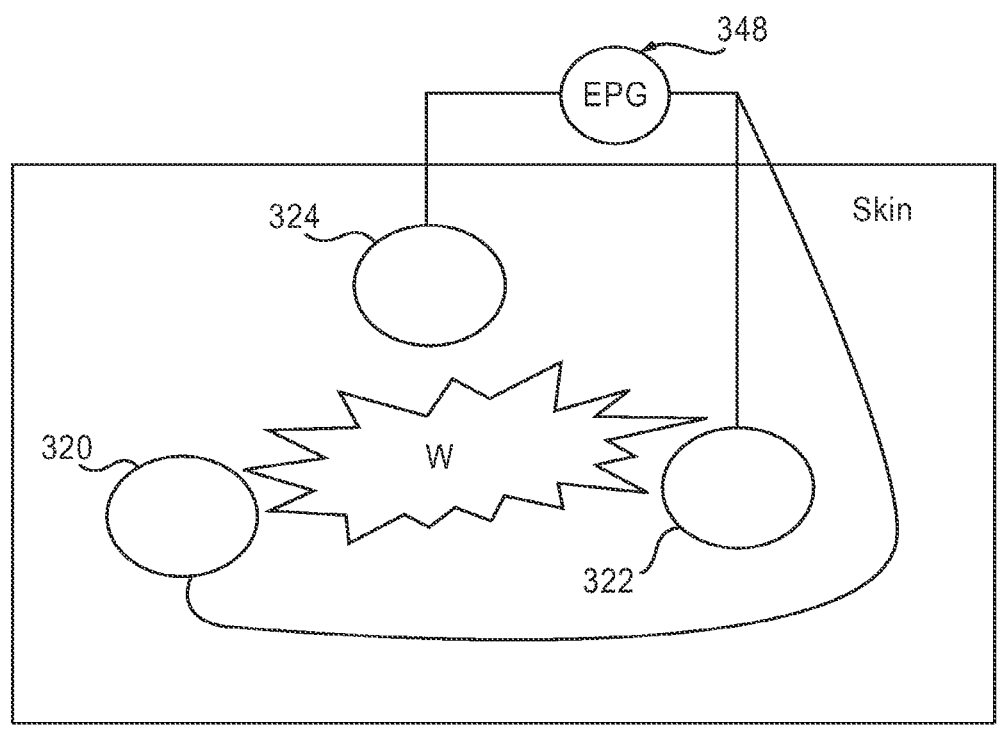
FIG. 11 is a top view of a schematic illustration of a system illustrating another application to treat a wound.
Figure 12:
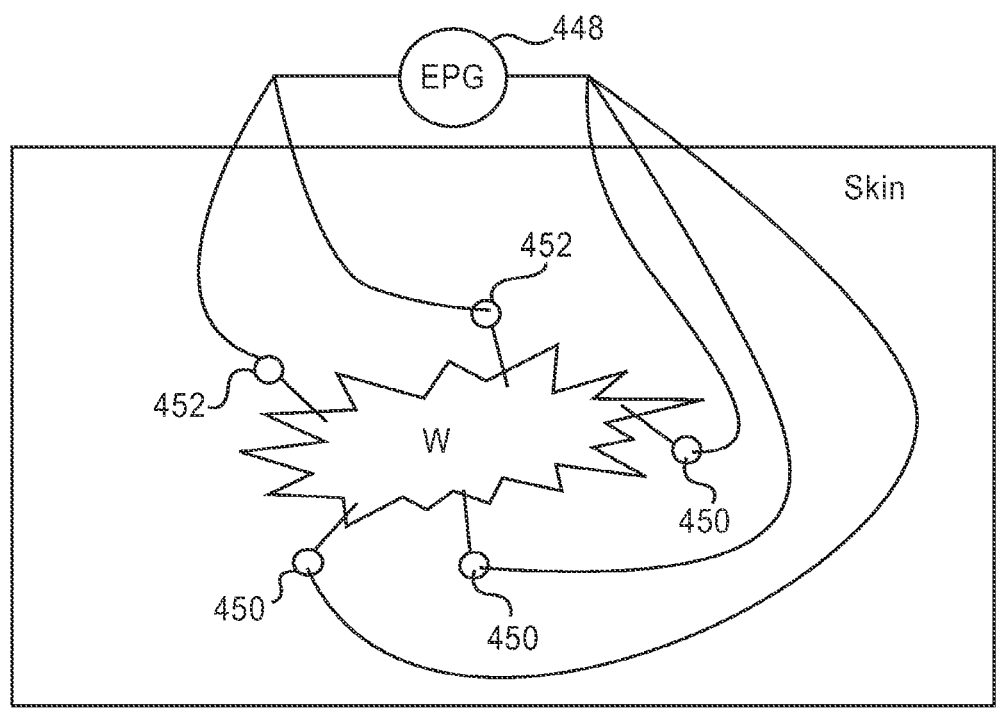
FIG. 12 is a top view of a schematic illustration of a system illustrating another application to treat a wound.

Electrical stimulation can be applied in several ways as illustrated in FIGS. 10-12. For example, as shown in FIG. 10, a first electrode 220 (positive or negative polarity) is applied to a sterile, conductive material, such as saline-moistened gauze pad 246 placed in the wound W. A conductive surface of a second electrode 222 is applied nearby on intact dry skin. An external pulse generator (EPG) 248 is connected to the first electrode (and gauze pad 246).

FIG. 11 is a top view illustrating an example application including positioning a conductive surface of each of two gel electrodes 320, 322 with the same polarity on intact dry skin on opposite borders of a wound W, such that they straddle the wound W. A third gel electrode 324 with the opposite polarity is placed nearby on intact dry skin. The first electrode 320 and the second electrode 322 are connected to a first terminal of an external pulse generator (EPG) 348, and the third electrode 324 is connected to a second terminal of the external pulse generator 348.

FIG. 12 is a top view illustrating an example application that includes positioning multiple electroacupuncture needles 450 and 452 around a perimeter of a wound W. In this embodiment, three electroacupuncture needles 450 are connected to a first terminal of an external pulse generator (EPG) 448 and have a first polarity, and two electroacupuncture needles 452 are connected to a second terminal of the external pulse generator 448 and have an opposite polarity. In each of the applications described and shown with reference to FIGS. 10-12, the pulse frequency can be, for example, set to about 100 pulses/second, and the voltage can be set, for example, to deliver a current that produces a moderately strong, but comfortable tingling sensation (in sensate skin) or a just-visible muscle contraction (in insensate skin, as in patients with spinal cord injuries).

The polarity of the electrode or electrodes placed in a straddling position around a wound, as shown in FIG. 11, can depend on the wound's clinical need. To promote autolysis, positive polarity may be desired to attract negatively charged neutrophils and macrophages. To encourage granulation tissue development, negative polarity may be desired to attract positively charged fibroblasts. To stimulate wound resurfacing, it may be desirable to use positive polarity to attract negatively charged epidermal cells.

Electrical stimulation with negative polarity can be used, for example, to improve collagen deposition in excisional wounds of diabetic and non-diabetic animals. Direct current (DC) stimulation can be used, for example, to reduce wound area more rapidly than alternating current (AC), but AC stimulation can reduce wound volume more rapidly than DC. Both DC and AC stimulation can cause significant increase of collagen content around experimental incisions and a similar result can arise using AC with switching polarities every second. DC currents of, for example, 50 to 300 µA can in some cases accelerate the rate of epithelialization, suggesting that electrical fields can influence the proliferative and/or migratory capacity of epithelial and connective tissue cells.

Figure 13:
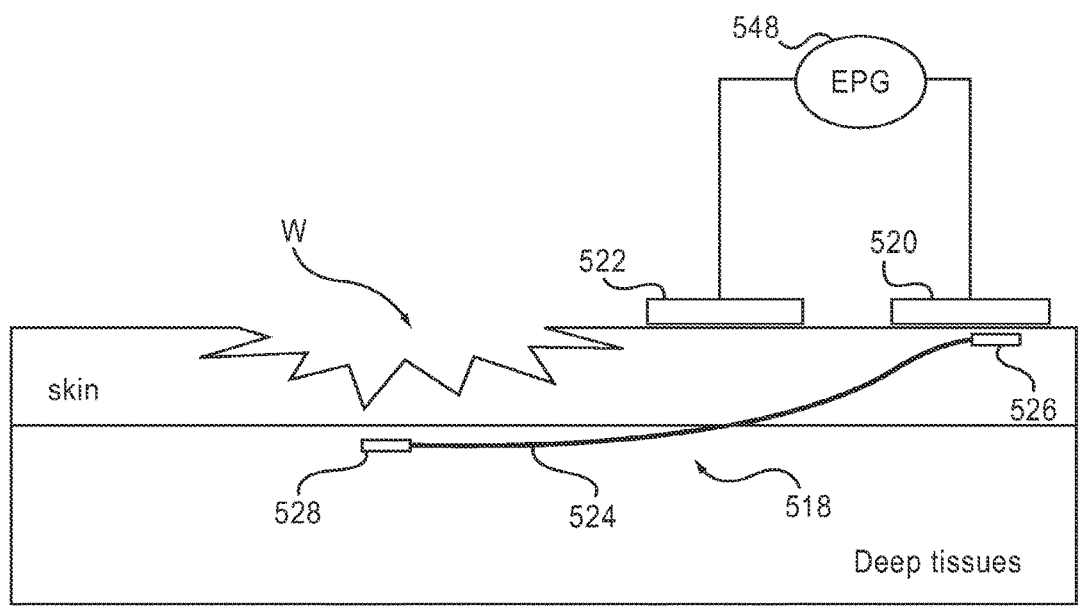
FIG. 13 is a side view of a schematic illustration of a system according to an embodiment illustrating an application to treat a wound.

Use of an implant as described herein for wound healing can provide several advantages over other known techniques. FIG. 13 illustrates one example use of an implant for wound healing. In this example, the electrical stimulation can be delivered through the wound by placing the stimulating end or stimulating electrode below or within the wound. As shown in FIG. 13, an implant 518 includes a conductor (e.g. lead) 524 that is connected on one end to a pick-up electrode 526 (i.e., pick-up end) and at another end to a stimulating electrode 528 (i.e., stimulating end). The stimulating electrode 528 is positioned beneath a wound W. An external cathodic electrode 520 and an external anodic electrode 522 are attached to the surface of the skin. An external pulse generator (EPG) 548 delivers electrical current to the external electrode 520 and a portion of the electrical current is picked-up by the pick-up electrode 526. The pick-up electrode 526 delivers the electrical current through the conductor 524 and to the stimulating electrode 528 located near the wound W. The stimulation returns from the stimulating electrode 528 to the EPG 548 via the wound W and the anodic electrode 522. Thus, electrical current passes through the wound W, stimulating deeper parts of the wound W.

Figure 14:
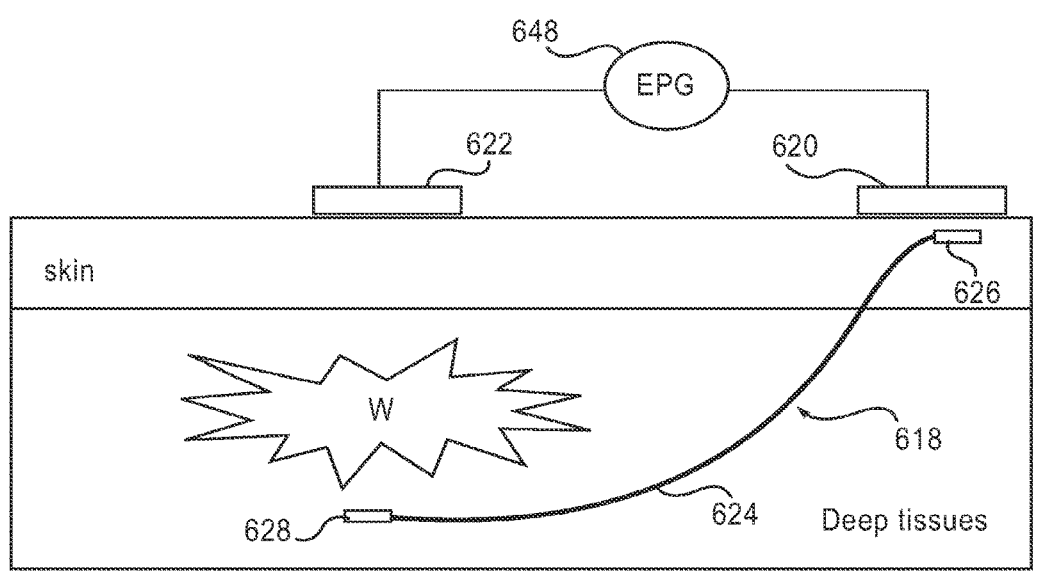
FIG. 14 is a side view of a schematic illustration of a system according to an embodiment illustrating an application to treat a deep wound.

FIG. 14 illustrates an example of a use of an implant where the stimulation is applied to deeper parts of a wound or to a deep or internal wound. As shown in FIG. 14, an implant 618 includes a conductor (e.g. lead) 624, a pick-up electrode 626 (i.e., pick-up end) connected to one end of the conductor 624 and a stimulating electrode 628 (i.e., stimulating end) connected to the other end of the conductor 618. The stimulating electrode 628 is positioned beneath a deep wound W. An external cathodic electrode 620 and an external anodic electrode 622 are attached to the surface of the skin. An external pulse generator (EPG) 648 delivers electrical current to the external electrode 620 and a portion of the electrical current is picked-up by the pick-up electrode 626. The pick-up electrode 626 delivers the electrical current through the conductor 624 and to the stimulating electrode 628 located near the wound W. As with the previous embodiment, the stimulation passes through the wound W, to the anodic electrode 622 and to the EPG 648. It also noted that other embodiments can include, for example, an additional implanted lead (e.g. conductor) on the other side of the wound with one terminal near the wound and the other terminal below the surface electrode 622.

In some embodiments, an implant can also be used in applications to enhance healing of fractures or breaks in bones and/or to promote bone growth. For example, bone in an area of a fracture can be electronegative with respect to the ephysis or diaphysis (relatively inactive areas of growth or repair). When the fracture is healed, the area of electronegativity has been found to be no longer observed. The region under compression of a bone that is, for example, bent, can be electronegative and the region under tension can be, for example, electropositive compared to the non-stressed portion of the bone. The production of electricity accompanying the stress is sometimes called the "piezoelectricity of bone." It has been observed that changes in environmental conditions (e.g., chemical, thermal, or mechanical) are first converted to electrical energy or stimuli that act on bone cells causing callus formation. The connection between the environmental stimulus and the callus is electricity, and therefore, the callus can be produced by electricity. Electrodes can be inserted into, for example, a medullary canal of a femur and a current can be applied such that over time, a ridge of callus is formed between the electrodes. Thus, greater new bone formation in the region of a negative electrode can be achieved.

In one example, a fracture in an ankle can be treated with electrical stimulation. For example, a cathodic electrode can be surgically inserted into the fracture site and an anodic electrode can be placed on the skin over the medial aspect of the foot. A constant electric current can then be applied to the cathodic electrode to deliver electrical stimulation to the fracture site. There are various modalities of electrical stimulation that can be used. For example DC stimulation, capacitive-coupled (or pulsed DC) stimulation, or pulsed electromagnetic filed stimulation (inductive coupled stimulation).

In an example of a DC stimulation (DC) application, multiple cathodic electrodes can be surgically inserted into a fracture site. The current source can be, for example, either implanted or external, or connected percutaneously to the implanted electrodes. An anodic electrode is placed on the skin close to the non-united (e.g. fractured or broken) site. The current carried by each cathodic electrode can vary depending on the material from which the cathodic electrode is made.

In another example application, capacitively coupled stimulation (CC) is applied in a non-invasive procedure. Electrodes are placed on either side of the fracture site. Windows are cut into a cast at the fracture site, if needed. An electrical field (e.g., 1-10 mV/cm) can be established in the tissue between the electrodes and the induced current is dispersed over a wide volume of tissue. The stimulation can be applied, for example, for 24 hours a day.

In an example using pulsed electromagnetic field (PEMF), an inductive coupling involving a time-varying magnetic field is applied. An electric field is produced when specific current waveforms are passed through coils placed around the fracture site. In some embodiments, two waveforms can be used, for example, pulsing electromagnetic fields and combined magnetic fields. With either waveform, voltage gradients (e.g., 1-10 mV) can be produced. The stimulation can be applied over a time period, for example, of 30 minutes to 10 hours per day.

Figure 15:
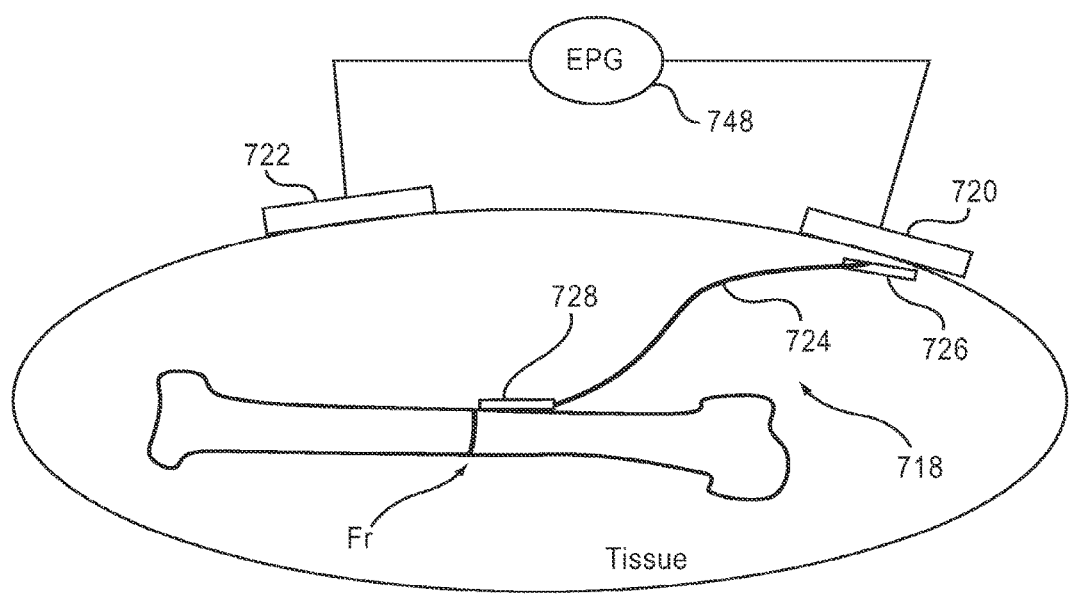
FIG. 15 is a side view of a schematic illustration of a system according to an embodiment illustrating an application to treat a bone fracture.

The use of an implant as described herein can provide a minimally invasive, efficient delivery of electrical stimulation to an area of a bone defect, such as a fracture or a break in a bone structure. As described for previous embodiments, and as illustrated in FIG. 15, an implant 718 includes a conductor 724, a pick-up electrode 726 and a stimulating electrode 728 that can be implanted under a patient's skin. The stimulating electrode 728 is positioned adjacent or in contact with a bone defect, such as fracture site Fr to be treated. An electrode 720 (e.g., a cathodic electrode or an anodic electrode) is positioned at an exterior location on the patient's skin and over the pick-up electrode 726. Another electrode 722 (e.g., the other of a cathodic electrode or anodic electrode) is positioned at a location on the patient's skin at a spaced distance from the electrode 720. The electrodes 720 and 722 can be, for example, gel electrodes.

An external pulse generator (EPG) 748 can be used to deliver electrical stimulation transcutaneously via the electrode 720. Part of the delivered stimulation is then picked up by the pick-up electrode 726 and is delivered to the stimulating electrode 728 implanted in the targeted area via the conductor 724.

The electrodes can be attached to a patient's skin out of the area covered by, for example, a case or cast disposed over a fracture site. In some embodiments, an opening is made in the cast, which will enable access to the skin and replacement of the electrodes, as desired. For example, it may be desirable to replace gel electrodes periodically. It is also possible to use wetted electrodes, which my be either replaceable or be attached between the cast and the skin. In such a case, periodic wetting of the electrodes may be performed via small openings in the cast.

In some embodiments, the case or cast can serve as an orthosis, carrying the electrodes and the EPG. For example, the stimulator (e.g., pulse generator) can be embedded within a cast or coupled to a cast that has been disposed over a broken or fractured limb (e.g., an arm or leg). An example of such an embodiment is described in U.S. Pat. No. 6,607,500, the disclosure of which is hereby incorporated by reference in its entirety.

Figure 16:
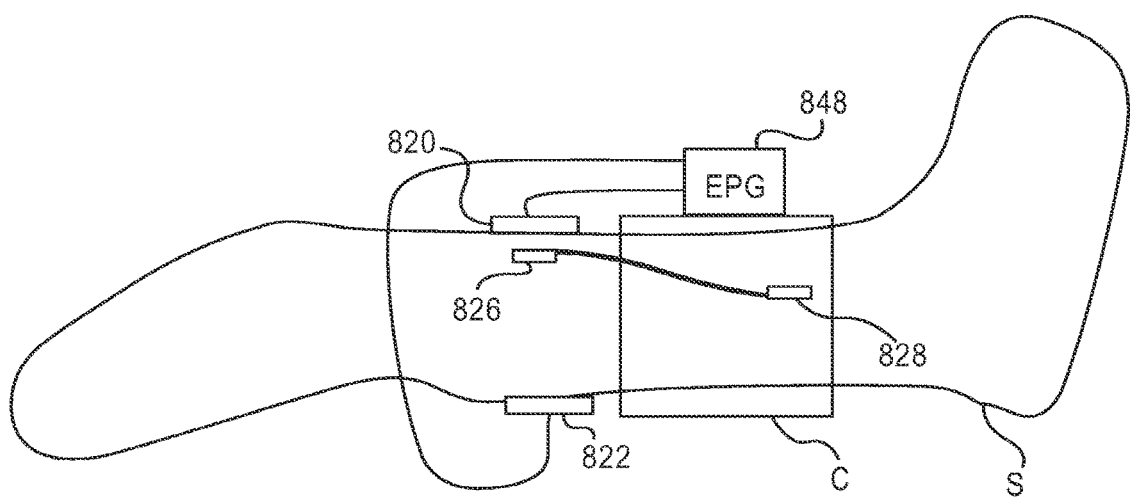
FIG. 16 is a side view of a schematic illustration of a system according to an embodiment illustrating an application to treat a bone defect and/or muscle.

FIG. 16 illustrates an embodiment of a system that includes a cast C disposed over a portion of a patient's anatomy, for example, over an area of a bone defect (not shown). In this embodiment, a system includes an implant 818 having a conductor 824 (e.g., lead), a pick-up electrode 826, and a stimulating electrode 828. An external pulse generator (EPG) 848 can be used to deliver electrical stimulation transcutaneously via the gel electrodes 820 and 822 attached to the skin S. As described above, a portion of the delivered stimulation is picked up by the pick-up electrode 826 and is delivered via the conductor 824 to the stimulating electrode 828 implanted in the targeted area. In this embodiment, the gel electrodes 820, 822 are attached to the skin out of the area covered by the case/cast C. In some situations, this can provide an advantage as compared to a standard TENS stimulation. For example, the external gel electrodes 820 and 822 can enable easy access and replacement being located outside the cast, while still delivering stimulation to the targeted location.

Thus, electrical stimulation has a variety of short-term therapeutic applications after injury or surgery as well as long-term applications for bone healing, or for prevention of muscle atrophy in paralyzed muscles as described above (see e.g., FIGS. 15 and 16).

Electrical stimulation can also be used in the treatment of headache and/or facial pain. Symptoms arising from headaches and/or facial pain are most commonly attributable to the trigeminal nerves located in the face or the nerves adjacent the upper cervical spine. Stimulation of such nerves can help to attenuate or control symptoms of headaches and/or facial pain. For example, the direct stimulation of such nerves can act as a "gate control" mechanism that can be used to attenuate or control symptoms. The trigeminal nerves and specific upper cervical spine nerves are associated with transmitting signals related to pain to the brain via their nerve fibers. Nociceptors (i.e., pain receptors) detect physiological changes in the body, such as pain, and send a signal to the brain, for example, via the trigeminal nerve or a specific upper cervical spine nerve. When one of these nerves is stimulated, the signal transmitted from the nociceptors can be substantially blocked from reaching the brain. More specifically, relatively low stimulation (e.g., less than about 100 Hz, or in some embodiments less than about 150 Hz) of one of these nerves can effectively activate the fibers of the nerve and compete (or "gate") with the nociceptive signals. Relatively high stimulation (e.g., more than about 100 HZ, or in some embodiments more than about 150 Hz) of one of these nerves can decrease excitement in the nerve fibers and effectively block the nociceptive signals by prohibiting transmission of the signal through the nerve fibers.

Figure 17:
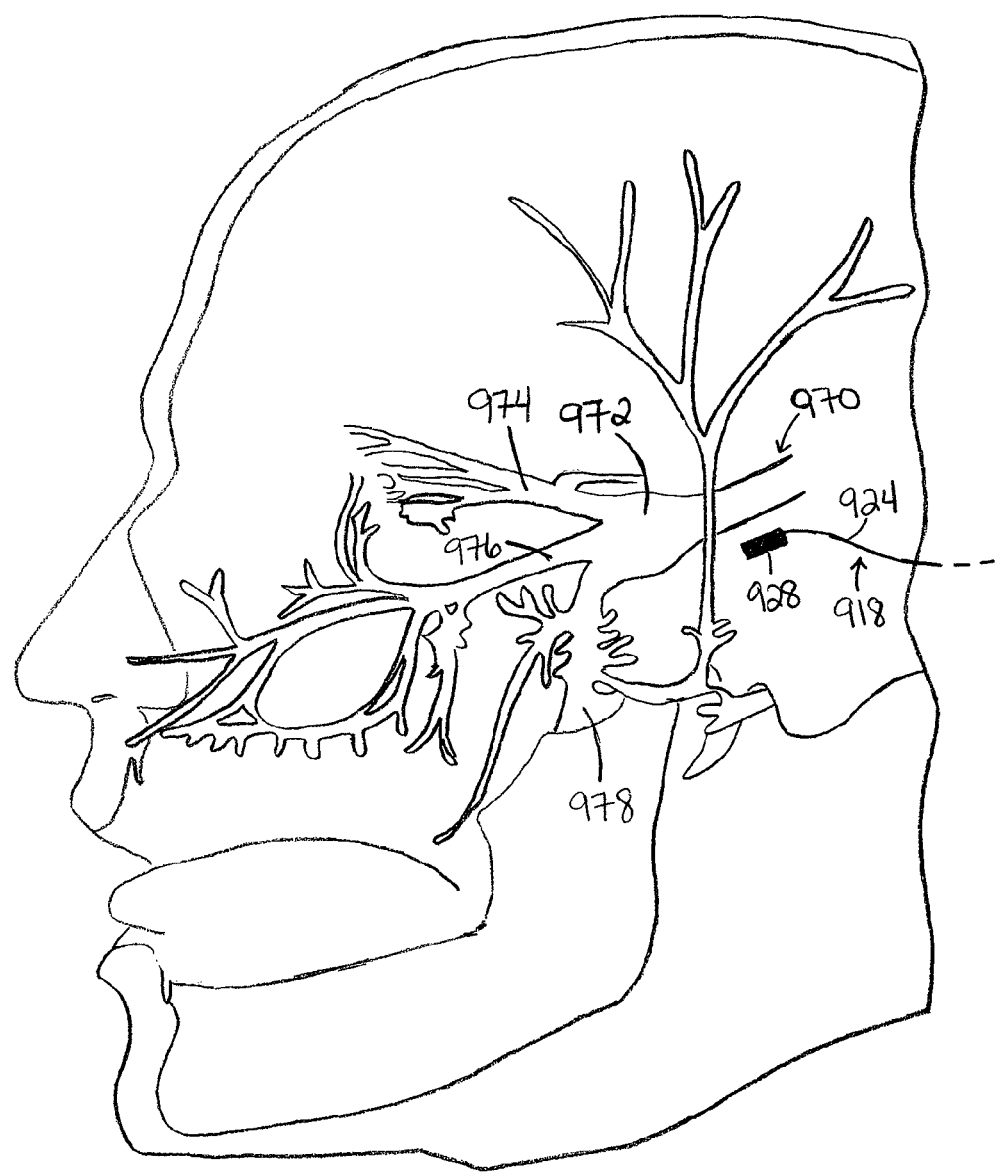
FIG. 17 illustrates the trigeminal nerve in the left side of a face and an implant according to an embodiment.

FIG. 17 illustrates one example of a use of an implant for treating headache and/or facial pain in a patient via stimulation of the left trigeminal nerve 970. In this example, the electrical stimulation can be delivered to the trigeminal nerve 970 in the left side of the face by placing the stimulating end or stimulating electrode adjacent to or on any portion of the trigeminal nerve 970. As shown in FIG. 17, an implant 918 includes a conductor (e.g., lead) 924 that is connected to a pick-up electrode (not shown in FIG. 17) and at another end to a stimulating electrode 928 (i.e., stimulating end). The stimulating electrode 928 is positioned adjacent to the trigeminal nerve 970. More specifically, the stimulating electrode 928 is positioned adjacent to the trigeminal ganglion 972 of the trigeminal nerve 970, as described in more detail herein. In some embodiments, the pick-up electrode is positioned subcutaneously behind the ear. It may be desirable for the pick-up electrode to be disposed beneath a substantially hairless region of skin located behind the ear. In this manner, a skin electrode or similar device can be disposed on the hairless region of skin over the pick-up electrode.

The trigeminal nerve 970 is responsible for a majority of the facial sensations. The face has two trigeminal nerves— one located in the right side of the face and the other located on the left side of the face (shown in FIG. 17). Many headaches, such as, migraines, tension-type headaches, chronic daily headaches, cluster headaches, and facial pain are attributable to the trigeminal nerve 970.

As shown in FIG. 17, the trigeminal nerve 970 includes a trigeminal ganglion 972, an opthalmic nerve 974, a maxillary nerve 976, and a mandibular nerve 978. The nerves 974, 976, and 978 of the trigeminal nerve 970, which are commonly referred to as "trigeminal branches," extend from the trigeminal ganglion 972. The trigeminal ganglion 972 contains sensory and nerve fibers that are distributed among each of the trigeminal branches. The opthalimic nerve 974 contains sensory fibers that carry sensory information to parts of the scalp, forehead, eyelid, eye, nose and blood vessels. The maxillary nerve 976 also contains sensory fibers that carry sensory information to parts of the cheek, lips, gums, sinuses and blood vessels. The mandibular nerve 978 contains both sensory and motor fibers. The sensory fibers of the mandibular nerve 978 carry sensory information to parts of the lip, teeth, gums, chin and jaw, including pain and temperature sensations from the mouth. The motor fibers of the mandibular nerve 978 carry motor information to the muscles involved in chewing and swallowing. Thus, any one of the trigeminal branches can cause symptoms of headaches and/or facial pain. As such, stimulation of any portion of these trigeminal branches and/or the trigeminal ganglion can reduce, eliminate or control symptoms of headaches and/or facial pain, as described above. Although this example illustrates the stimulation of the left trigeminal nerve 970, it should be understood that the right trigeminal nerve can be stimulated and achieve similar results for symptoms specific to the right side of the face.

Although not shown in FIG. 17, it should be understood that external (i.e., surface) electrodes (not shown in FIG. 17) can be attached to the surface of the skin as described above for previous embodiments. An external pulse generator (not shown in FIG. 17) can deliver electrical current to the external electrode(s) and a portion of the electrical current can be picked up by a pick-up electrode (not shown in FIG. 17). As discussed above, the external electrode(s) can be disposed on the surface of the skin above the pick-up electrode and in a hairless region behind the ear. The pick-up electrode can then deliver the electrical current through the conductor 924 and to the stimulating electrode 928 located adjacent the trigeminal ganglion 972 of the trigeminal nerve 970. The stimulation returns from the stimulating electrode 928 to the external pulse generator via the trigeminal nerve 970 and the surface electrode(s). Thus, electrical current passes through and stimulates the trigeminal ganglion 972 of the trigeminal nerve 970. In some embodiments, stimulation can be delivered via the external pulse generator at less than about, for example, 100 Hz to activate the trigeminal nerve 970. In some embodiments, stimulation can be delivered at less than about, for example, 150 Hz. In other embodiments, stimulation can be delivered via the external pulse generator at greater than 100 Hz or greater than 150 Hz to block neural activity in the trigeminal nerve 970.

Although the stimulating electrode 928 in FIG. 17 is illustrated and described above as being adjacent to the trigeminal ganglion 972 of the trigeminal nerve 970, it is to be understood that the stimulating electrode 928 can be adjacent to or in contact with any portion of the trigeminal nerve 970. Said another way, the stimulating electrode 928 can be adjacent to or in contact with any portion of the opthalmic nerve 974, the maxillary nerve 976, and/or the mandibular nerve 978. Stimulation of any of these trigeminal branches can result in attenuation or control of headache and/or facial pain symptoms.

Figure 18:
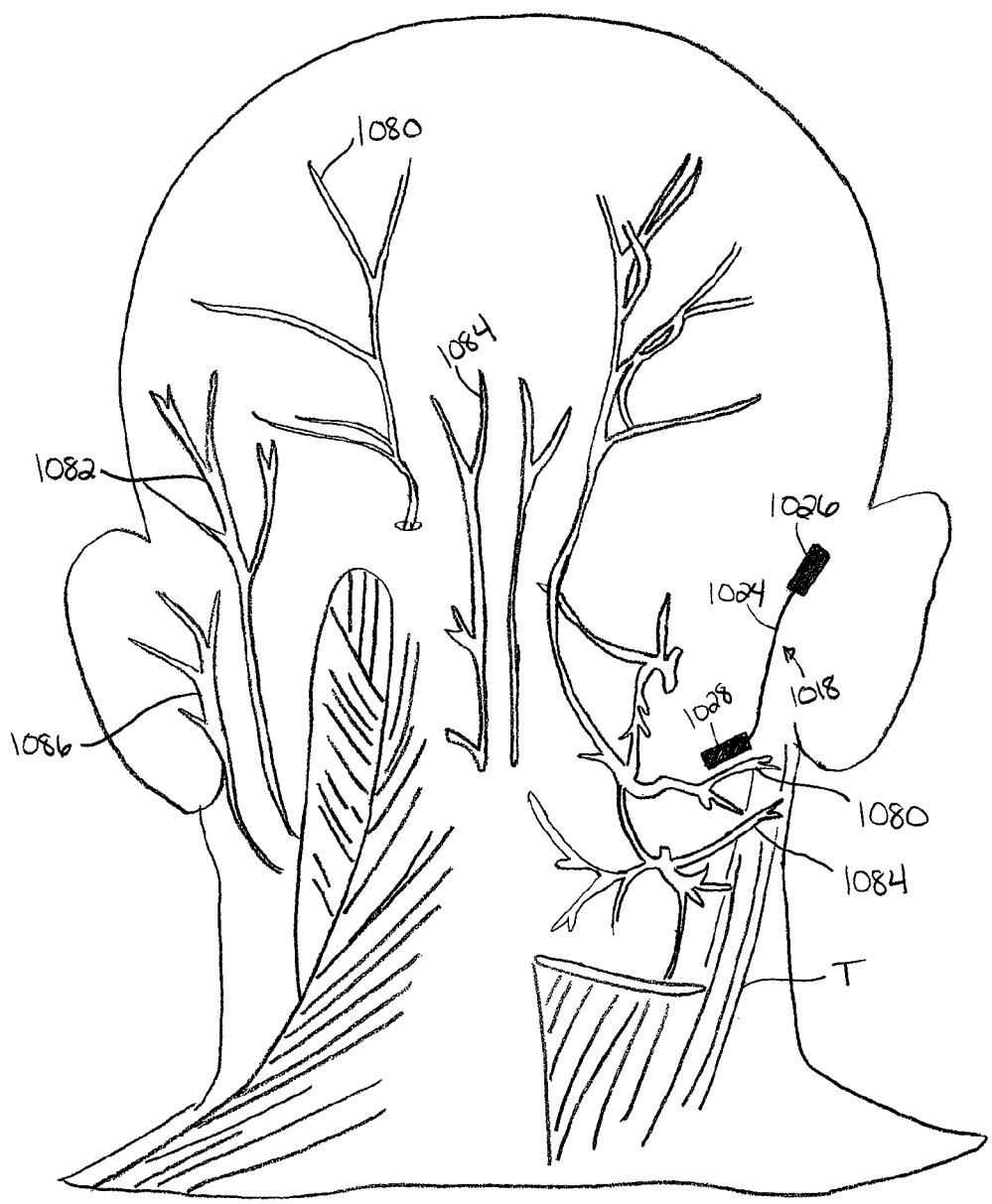
FIG. 18 illustrates an area adjacent the upper cervical spine and an implant according to an embodiment.

FIG. 18 illustrates another example use of an implant for treating headache and/or facial pain in a patient via stimulation of a nerve adjacent the upper cervical spine. In this example, the electrical stimulation can be delivered to the greater occipital nerve 1080, which is adjacent the upper cervical spine (C1-C4), by placing the stimulating end or stimulating electrode adjacent to or in contact with any portion of the greater occipital nerve 1080. The greater occipital nerve 1080, which converges with the trigeminal nerve at the spinal cord, is an easily accessible spinal nerve located subcutaneously in the back of the head or side of the neck. Disorders associated with the greater occipital nerve 1080 can cause headaches, such as, for example, cervicogenic headaches (i.e., occipital neuralgias). Such headaches originate in the neck area (due to the location of the greater occipital nerve 1080) and often include symptoms associated with tension-type headaches, migraines and cluster headaches. Other nerves similarly located adjacent the upper cervical spine and associated with headache and/or facial pain symptoms include the lesser occipital nerve 1082, the third occipital nerve 1084, the greater auricular nerve 1086, the transverse cervical nerve (not shown in FIG. 18), the supraclavicular nerve (not shown in FIG. 18), and/or any portion thereof.

As shown in FIG. 18, an implant 1018 includes a conductor (e.g., lead) 1024 that is connected to a pick-up electrode 1026 and at another end to a stimulating electrode 1028 (i.e., stimulating end). The pick-up electrode 1026 can be positioned, for example, subcutaneously behind the ear of the patient, and beneath a region of skin that is substantially hairless, as described above with reference to the previous embodiment. In some embodiments, the pick-up electrode 1026 can be positioned on the superior portion of the temporal bone, the anterior portion of the temporal bone or the mastoid portion of the temporal bone (e.g., a portion of the mastoid process). In some embodiments, the hairless region of skin located above the pick-up electrode 1026 can have a diameter of at least 2 cm. In this manner, a skin electrode or a similar device can be disposed on the hairless region of skin above the pick-up electrode 1026.

The stimulating electrode 1028 is positioned adjacent to the greater occipital nerve 1080. In some embodiments, however, the stimulating electrode 1028 can be positioned directly in contact with the greater occipital nerve 1080. Although not shown in FIG. 18, in some embodiments, the stimulating electrode 1028 can be positioned parallel to the greater occipital nerve 1080 at a location along the superior nuchal line of the occipital bone (not shown in FIG. 18) where the greater occipital nerve 1080 is superficial to the trapezium muscle, T. The occipital bone is the lower portion of the cranium, which has a series of nuchal lines (i.e., curved lines on its external surface) including the superior nuchal line. The trapezium muscle, T, is attached to and extends from the occipital bone.

Although not shown in FIG. 18, it should be understood that external (i.e., surface) electrodes (not shown in FIG. 18) can be attached to the surface of the skin as described above for previous embodiments. An external pulse generator (not shown in FIG. 18) can deliver electrical current to the external electrode(s) and a portion of the electrical current can be picked up by the pick-up electrode 1026. The pick-up electrode 1026 can then deliver the electrical current through the conductor 1024 and to the stimulating electrode 1028 located adjacent the greater occipital nerve 1080. The stimulation returns from the stimulating electrode 1028 to the external pulse generator via the greater occipital nerve 1080 and the surface electrode(s). Thus, electrical current passes through and stimulates the greater occipital nerve 1080. In some embodiments, stimulation can be delivered via the external pulse generator at less than approximately 100 to 150 Hz to activate the greater occipital nerve 1080. In other embodiments, stimulation can be delivered via the external pulse generator at greater than approximately 100 to 150 Hz to block neural activity in the greater occipital nerve 1080. As discussed above, such stimulation is particularly effective in patients suffering from cervicogenic headaches.

Although the stimulating electrode 1028 is illustrated and described above as being adjacent to and used to stimulate the greater occipital nerve 1080 located in the upper cervical spine, in other embodiments, the stimulating electrode 1028 can be adjacent to and used to stimulate another nerve adjacent the upper cervical spine. Such nerves can include, for example, the lesser occipital nerve 1082, the third occipital nerve 1084, the greater auricular nerve 1086, the transverse cervical nerve (not shown), the supraclavicular nerve (not shown), and/or any portion thereof. Stimulation of any of these nerves can help alleviate and/or control symptoms of headaches and/or facial pain in the same manner described above.

In some embodiments, the stimulating electrode 1028 (i.e., the stimulation portion of the implant 1018) can be implanted within the patient through an incision located approximately 3 cm to 4 cm inferior to or superior to the superior nuchal line of the occipital bone. In some such embodiments, the stimulating electrode 1028 can be implanted using minimally invasive techniques after confirming physiological responses with an active stimulation probe.

Although implants 918 and 1018 are illustrated and described above as being unilateral implants, in other embodiments, implants 918 and 1018 can be bilateral implants. In this manner, a bilateral implant can include two leads, two separate implantations and/or two external pulse generators.

Electrical stimulus can also be used in the prevention of deep venous thrombosis. During periods of immobilization, it can be important to continue to contract the limb muscles to move the venous blood back to the heart and to prevent pooling of the blood. This is especially applicable after pelvic fractures, as well as after total hip or knee replacements. If there is pooling of blood in the legs, a blood clot or thrombus formation can result in a small portion of the clot (emboli) breaking off. The emboli can lodge in the lungs resulting in pulmonary embolism and possible death. Electrical stimulation can be used to prevent the blood from pooling by frequent contraction of the muscles (for example the calf muscles). In addition to the creation of a muscle pump, electrical stimulation may increase plasma fibrinolytic activity and reduce the potential of clotting.

Electrical stimulation can also be used in the management of stiffness and joint contractures after immobilization. Electrical stimulation can provide several benefits in the rehabilitation of stiff joints. Electrical stimulation can be used to augment contraction of the muscles and hold the contraction at the end of the available joint range. Electrical stimulation can modulate discomfort or pain during the early mobilization period, and can enhance the force production, work capability and endurance of the stimulated muscles. Severe muscle atrophy can occur rapidly following traumatic spinal cord injury. In such a case, electrical stimulation may be beneficial in preventing secondary impairments of patients with spinal cord injuries when applied before extensive post-injury atrophy occurs.

As described above, electrical stimulation can also be used in the management of joint and arthritis pain. For example, electrical stimulation can reduce pain and/or other symptoms associated with osteoarthritis (e.g., of the knee) or rheumatoid arthritis (e.g., of the hand). More specifically, electrical stimulation can significantly decrease chronic musculoskeletal pain. Electrical stimulation can be applied to the affected joint directly and/or to the muscle tissue adjacent the joint in a similar manner as described herein for stimulation of other areas of the body of a patient. Stimulation of the muscle tissue adjacent the joint can effectively strengthen that muscle so that it better supports the joint, thereby reducing pain in and around the joint. As discussed above, stimulation of the joint and/or adjacent muscle tissue can alleviate or control pain so that complicated and invasive surgeries, such as, for example, total or partial knee replacements, can be delayed or completely avoided.

Electrical stimulation can also be used in the management of muscle performance. For example, electrical stimulation of a muscle or of a nerve innervating the muscle may be applied to maintain muscle contractility during periods of immobilization when the effect of muscle contraction would not interfere with the healing. Although electrical stimulation during immobilization may not completely prevent shrinkage or atrophy of muscle, it may minimize the loss and maintain the metabolic capability of muscle to speed recovery when it is safe to resume movement and exercise. When the resumption of exercise is permitted after injury or surgery, electrical stimulation may be used to provide sensory input and to improve muscle recruitment.

In a situation where a nerve block (neuropraxia) is present, electrical stimulation may be used to maintain the paralyzed muscle until the nerve block resolves. Depending on the location of the weak or paralyzed muscles, electrical stimulation may be used to substitute a brace or orthosis. In some embodiments, augmentation of muscle strength with electrically elicited muscle contractions can occur in a similar manner to augmentation of muscle strength with voluntary exercise. In some cases, augmentation of muscle strength using percutaneous stimulation is fundamentally different from augmentation of strength with voluntary exercise.

Electrical stimulation can be delivered transcutaneously, percutaneously or using fully implanted stimulators. In one example, electrical stimulation includes the use of electrical stimulation of quadriceps femoris and hamstring muscle groups during a period of low extremity cast immobilization for an athlete who sustained grade II medial, collateral and anterior cruciate ligament sprains. Three weeks after cast removal, single-leg, vertical-leap height was 92% of that accomplished by the dominant, uninjured leg, and the patient was able to return to athletic competition. This example illustrates that electrical stimulation may attenuate denervation and age-related muscle atrophy. In another example, electrical stimulators were implanted in rats, stimulating the extensor digitorum longus. This example illustrates that electrical stimulation can be used to reduce age-related atrophy and weakness by ensuring that all of the muscle fibers underwent titanic contraction. In another example, percutaneous electrical stimulation can be used in preventing immobilization-induced muscle atrophy. In some cases, brief periods of percutaneous electrical stimulation can reduce quadriceps atrophy secondary to knee immobilization, and can aid in the prevention of the fall in muscle protein synthesis that usually occurs on immobilization. In some cases, electrical stimulation can prevent a fall in oxidative enzyme activity.

Each of the above described procedures can also be performed using a miniature implantable stimulator(s) for delivery of the electrical stimulation in a patient. Such miniature implantable electrical stimulators are described in U.S. Pat. Nos. 6,735,475, 6,941,171 and 6,735,474, each of the disclosures of which is hereby incorporated by reference in its entirety.

For example, a miniature implantable electrical stimulator(s) can be used in conjunction with a joint replacement procedure to improve patient healing and decrease pain. A miniature implantable stimulator has several advantages compared to other techniques, for example, as follows. Compared with a transcutaneous device, with a miniature implantable electrical stimulator, an electrical stimulation can be delivered to a specific location (e.g. to the specific nerve), with no unpleasant sensation from cutaneous receptors, due to delivery of the stimulation thru the skin. There are also no external gel electrodes, which may cause skin irritation and require replacement and/or re-alignment. As with the stimulation systems and implants described above, compared with percutaneous stimulation, with a miniature implantable electrical stimulator, the risk of inflammation or contamination due to the lead protruding thru the skin can be reduced or eliminated. Also, compared to a full size implantable stimulator, with a miniature implantable electrical stimulator, only a minimally invasive procedure is typically required.

Miniature implantable electrical stimulator(s) used in conjunction with a joint replacement procedure can also be used to delay or defer the need for a joint replacement procedure as described above. Conditioning of the muscles/joint can be done before a joint replacement procedure (e.g. increasing range of motion). Improvements can be made in pain management and/or in management of muscle performance. In some cases, stimulation of a joint can also help prevent deep venous thrombosis. It is also noted that the use of electrical stimulation based on implanted passive conductors as described herein can have benefits similar to those of miniature stimulators, while providing a significantly less expensive alternative.

While various embodiments have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

Although various embodiments have been described as having particular features and/or combinations of components, other embodiments are possible having a combination or sub-combination of any features and/or components from any of the embodiments described herein. For example, one or more of the implants (e.g., 18, 118, 118', 518, 618, 718, 818, 918, 1018) can be used in a procedure to stimulate a bodily tissue (e.g., soft tissue, muscle, ligaments, bone structures, etc.). Thus, in any procedure described herein, although not necessarily illustrated, a second implant can be included, such as shown in FIG. 1 (e.g., including return conductor 34). It is also noted that any embodiment of an implant can be used for any of the various procedures described herein. For example, an implant can be used for any of the above-described procedures with or without a cuff electrode (as described in FIG. 1).

Further, the quantity of electrodes can vary depending on the particular treatment. The type of electrode can also vary, for example, a plate electrode or a cuff electrode can be used. Although some embodiments describe applying or delivering electric current from a stimulator (e.g., pulse generator) to a cathodic electrode attached to a surface of a patient over the pick-up end or pick-up electrode of an implant, it should be understood, that an anodic electrode can alternatively be placed over the pick-up end or pick-up electrode and electrical current delivered thereto. For example, as described with reference to FIGS. 5-8, various configurations and combinations of cathodic electrodes and anodic electrodes (e.g., positioning relative to the implanted conductor) can be used.

Further, the various components of an implant as described herein can have a variety of different shapes and or size not specifically illustrated. For example, the terminations (e.g., 30), the conductors (e.g., 24, 124, etc.), the pick-up end or pick-up electrode (e.g., 26, 126, etc.), the stimulating ends or stimulating electrodes (also referred to as delivering ends or electrodes) (e.g., 28, 128, etc.) can each have a variety of different shapes sizes, cross-sections, thickness, etc. In addition, the electrodes (e.g., 20, 22, 120, 122, etc.), can be a variety of different shapes, sizes, types, etc. Although a stimulator for delivering electric current to the electrodes was described as a pulse generator, in some embodiments, other types of stimulators can alternatively be used. Various power sources can also be used, including for example, a wireless or wired connection to the stimulator.

What is claimed is:

1. A method for electrically stimulating a tissue in proximity to a joint in a subject, comprising:
implanting a first implant in the subject's body, the first implant including a passive electrical conductor having a pick-up portion and a delivery portion;
implanting a second implant in the subject's body, the second implant including a passive electrical conductor having a pick-up portion and a delivery portion;
positioning the electrode array on the body such that (1) the first surface cathodic electrode is positioned over the pick-up portion of the electrical conductor of the first implant, (2) the first surface anodic electrode of the electrode array is positioned over the delivery portion of the electrical conductor of the first implant, (3) the second surface cathodic electrode is positioned over the pick-up portion of the electrical conductor of the second implant, and (4) the second surface anodic electrode of the electrode array is positioned over the delivery portion of the electrical conductor of the second implant, the electrode array configured to receive an electric current from a stimulator,
the pick-up portion of the electrical conductor of the first implant being configured to pick up at least a portion of the electric current from the first surface cathodic electrode and to transmit the portion of the electric current to the delivery portion of the first implant for delivery of the portion of the electric current to a first tissue in proximity to a joint,
the pick-up portion of the electrical conductor of the second implant being configured to pick up at least a portion of the electric current from the second surface cathodic electrode and to transmit the portion of the electric current to the delivery portion of the second implant for the delivery of the portion of the electric current to a second tissue in proximity to a joint; and
applying the electric current via the electrode array to cause the portion of the electric current to flow through the first implant to be delivered to the first tissue in proximity to the joint and to cause the portion of the electric current to flow through the second implant to be delivered to the second tissue in proximity to the joint.

2. The method of claim 1, wherein the applying the electric current includes stimulation sufficient to improve mobility of the joint and to treat joint pain.

3. The method of claim 1, wherein the applying includes, applying at least one of direct, pulsatile or alternating electric current between the first surface cathodic electrode and the first surface anodic electrode.

4. The method of claim 1, wherein the joint is a knee joint.

5. The method of claim 1, wherein the applying electric current to the joint includes stimulation of the joint sufficient to treat at least one of joint pain or arthritis.

6. The method of claim 1, wherein:
the pick-up portion of the first implant forms an electrical termination having a sufficient surface area such that, once implanted in subcutaneous tissue below the surface cathodic electrode, the first portion of the electric current flows through the conductor of the first implant, in preference to flowing through body tissue between the first surface cathodic electrode and the first surface anodic electrode, and
the delivery portion of the first implant forms an electrical termination to deliver the first portion of the electric current to the joint, once implanted.

7. The method of claim 1, wherein the applying electric current to the joint includes stimulation of the joint at a frequency within the range of 1 Hz and 100 Hz.

8. The method of claim 1, wherein the applying electric current to the joint includes stimulation of the joint at a frequency greater than 30 Hz and less than 50 Hz.

9. A method for electrically stimulating a nerve in a subject, comprising:
disposing a first end of a first implant under a subject's skin at a first location;
disposing a second end of the first implant under the subject's skin at a second location at a non-zero distance from the first end of the first implant in proximity to a first nerve of the patient, the first implant including a passive electrical conductor extending under the subject's skin between the first end and the second end;
disposing a first end of a second implant under the subject's skin at a third location;
disposing a second end of the second implant under the subject's skin at a fourth location at a non-zero distance from the first end of the second implant in proximity to a second nerve of the patient, the second implant including a passive electrical conductor extending under the subject's skin between the first end and the second end;
placing a first surface electrode on an exterior surface of the subject's skin at a first location, the first location on the exterior surface of the subject's skin being above the first location under the subject's skin;
placing a second surface electrode on an exterior surface of the subject's skin at a second location, the second location on the exterior surface of the subject's skin being above the second location under the subject's skin, the second surface electrode being spaced apart from the first surface electrode;
placing a third surface electrode on an exterior surface of the subject's skin at a third location, the third location on the exterior surface of the subject's skin being above the fourth third location under the subject's skin, the third surface electrode being spaced apart from each of the first surface electrode and the second surface electrode;
placing a fourth surface electrode on an exterior surface of the subject's skin at a fourth location, the fourth location on the exterior surface of the subject's skin being above the fourth location under the subject's skin; and
delivering an electric current to the first surface electrode and the third surface electrode such that a portion of the electric current is picked up by the first end of each of the first implant and the second implant, through the conductor of each of the first implant and the second implant, to the second end of each of the first implant and the second implant and into the first nerve and the second nerve, respectively, to simulate the at least one of the first nerve and the second nerve, at least a portion of the electric current being transmitted, during the delivering, through body tissues extending between each of the first nerve and the second nerve and subcutaneous tissue located below each of the second surface electrode and the fourth surface electrode, respectively.

10. The method of claim 9, wherein the delivering includes delivering at least one of direct, pulsatile or alternating electric current between the first surface electrode and the second surface electrode.

11. The method of claim 9, wherein the first nerve is one of the common peroneal nerve or the tibial nerve.

12. The method of claim 9, wherein the second nerve is one of the common peroneal nerve or the tibial nerve.

13. The method of claim 9, wherein the delivering the electric current includes stimulation of at least one of the first nerve or the second nerve sufficient to treat at least one of joint pain or arthritis.

14. The method of claim 9, wherein the delivering the electric current includes stimulation of at least one tissue in proximity to at least one of the first nerve or the second nerve sufficient to improve mobility of a joint.

15. The method of claim 9, wherein the first surface electrode is a cathodic electrode, the second surface electrode is an anodic electrode, the third surface electrode is a cathodic electrode, and the fourth surface electrode is an anodic electrode.

16. The method of claim 9, wherein the first surface electrode is an anodic electrode, the second surface electrode is a cathodic electrode, the third surface electrode is an anodic electrode, and the fourth surface electrode is a cathodic electrode.

17. The method of claim 9, wherein a first distance between the first surface electrode and the second surface electrode on the exterior surface of the subject's skin is different than a second distance between the first surface electrode and the third surface electrode on the exterior surface of the subject's skin.

18. The method of claim 17, wherein the second distance is greater than the first distance.

\* \* \* \* \*

UNITED STATES PATENT AND TRADEMARK OFFICE
CERTIFICATE OF CORRECTION

PATENT NO. : 9,925,374 B2  
APPLICATION NO. : 13/000840  
DATED : March 27, 2018  
INVENTOR(S) : Arkady Glukhovsky et al.

Page 1 of 1

It is certified that error appears in the above-identified patent and that said Letters Patent is hereby corrected as shown below:

In the Claims

Column 26, Line 51 (Claim 9, Line 33): delete "fourth".

Signed and Sealed this
Twentieth Day of November, 2018

Andrei Iancu
*Director of the United States Patent and Trademark Office*